US005698394A

United States Patent [19]

Duhamel et al.

[11] Patent Number: 5,698,394

[45] Date of Patent: Dec. 16, 1997

[54] NUCLEOTIDE SEQUENCES AND METHODS FOR DETECTION OF *SERPULINA HYODYSENTERIAE*

[75] Inventors: Gerald E. Duhamel; Robert Elder, both of Lincoln, Nebr.

[73] Assignee: Board of Regents of the University of Nebraska, Nebr.

[21] Appl. No.: 252,492

[22] Filed: Jun. 1, 1994

[51] Int. Cl.$^6$ .............................. C12P 19/34; C12Q 1/68; C07H 21/02; C07H 21/04

[52] U.S. Cl. .............................. 435/6; 435/9.12; 536/24.3; 536/24.31; 536/24.33

[58] Field of Search .............................. 435/6, 91.2; 536/24.3, 536/24.31, 24.32

[56] References Cited

U.S. PATENT DOCUMENTS

| | | | |
|---|---|---|---|
| 4,683,202 | 7/1987 | Mullis | 435/91 |
| 4,748,019 | 5/1988 | Lysons | 424/92 |
| 4,764,370 | 8/1988 | Fields et al. | 424/93 |
| 4,818,680 | 4/1989 | Collins et al. | 424/92 |
| 4,851,331 | 7/1989 | Vary et al. | 435/6 |
| 4,999,191 | 3/1991 | Glisson et al. | 424/92 |
| 5,034,315 | 7/1991 | Jensen et al. | 435/6 |
| 5,298,392 | 3/1994 | Atlas et al. | 435/6 |
| 5,306,616 | 4/1994 | Lupski et al. | 435/6 |

FOREIGN PATENT DOCUMENTS

| | | |
|---|---|---|
| 0 282 965 | 9/1988 | European Pat. Off. . |
| 0 350 715 | 1/1990 | European Pat. Off. . |
| WO 88/04778 | 6/1988 | WIPO . |
| WO 90/02565 | 3/1990 | WIPO . |
| WO 91/04036 | 4/1991 | WIPO . |

OTHER PUBLICATIONS

Achacha et al., *J. Vet. Diag. Invest.*, 3:211–214 (1991) is cited in the specification at p. 3, line 27–28.

Baum and Joens, *Infect. Immun.*, 25:792–796 (1979) is cited in the specification at p. 2, line 3.

Belanger et al., *J. Clin. Microbiol.*, 29:1727–1729 (1991) is cited in the specification at p. 3, lines 28–29 and p. 4, line 1.

Boyden et al., "Cloning and Characterization of *Treponema hyodysenteriae* Antigens and Protection in a CF-1 Mouse Model by Immunization with a Cloned Endoflagellar and Antigen", *Infect. Immun.*, 57:3808–3815 (1989) is cited in the specification at p. 5, lines 11–12.

Burrows and Lemcke, *Vet. Rec.*, 108:187–189 (1981) is cited in the specification at p. 4, line 2 and lines 14–15.

Caputa et al., *J. Clin. Microbiol.*, 29:2418–2413 (1991) is cited in the specification at page 47, line 25–26.

Chenngappa et al., "Laboratory Procedures for the Diagnosis of Swine Dysentary", *Report of the Committee on Swine Dysentery*, American Association of Veterinary Laboratory Diagnosticians, Committee on Swine Dysentery, Aug. (1989) is cited in the specification at p. 2, lines 10–13.

Chien et al., *J. Bacteriol.* 127:1550 (1976) is cited in the specification at p. 27, lines 20–21.

Combs and Hampson, *Res. Vet. Sci.*, 50:286–289 (1991) is cited in the specification at p. 5, line 26.

Curtiss III et al., *Infection and Immunity*, 55:3035 (1987) is cited in the specification at p. 37, line 18.

Cwyk et al., *Arch. Microbiol.*, 122:231–239 (1979) is cited in the specification at p. 45, line 27.

Dougan et al., *J. Infec. Dis.*, 158:1329 (1988) is cited in the specification p. 37, line 19.

Duhamel et al., *J. Vet. Diagn. Invest.*, 4:285–292 (1992) is cited in the specification at p. 58, line 35 and p. 63, line 33.

Edwards et al., *J. Bacteriol.*, 170:3991 (1988) is cited in the specification at p. 37, lines 19–20.

Elder et al., *J. Clin. Micro.*, 32:1497 (1994) is cited in the specification at p. 16, line 29; p. 22, line 18–19; p. 27, line 33; and p. 63, line 6 and line 34.

Fisher and Olander, *Am. J. Vet. Res.*, 46:450–455 (1981) is cited in the specification at p. 2, line 27.

Flores et al., "Identification of Human Rotavirus Serotype by Hybridization to Polymerase Chain Reaction–Generated Probes Derived from a Hyperdivergent region of the Gene Encoding Outer Capsid Protein VP7", *J. Virol.*, 64:4021–4024 (1990) is cited in the specification at p. 20, lines 11–12.

Harris and Lysons, *Diseases of Swine*, 7th ed., Iowa State University Press (Ames, IA), at pp. 599–616 (1992) is cited in the specification at p. 1, line 34–35.

Kinyon and Harris, *Int. J. Syst. Bact.*, 29:102–109 (1979) is cited in the specification at p. 2, line 18; p. 44, line 23; and p. 45, lines 2–3.

Hopp et al., *Mol. Immunol.*, 20:483 (1983) is cited in the specification at p. 62, line 8.

Hugo et al., *J. Clin. Microbiol.*, 25:26–30 (1987) is cited in the specification at p. 61, lines 1–2, lines 22–23, and lines 30–31.

Hunter et al., *Vet. Rec.*, 104:383–384 (1979) is cited in the specification at p. 3, lines 29–30.

Islam et al., "Detection of *Shigella dysenteriae* Type 1 and *Shigella flexneri* in Feces by Immunomagnetic Isolation and Polymerase Chain Reaction", *J. Clin. Micro.*, 30:2801–2806 (1992) is cited in the specification at p. 27, lines 11–12 and p. 28, lines 20–21.

(List continued on next page.)

*Primary Examiner*—George C. Elliott
*Assistant Examiner*—Jeffrey Fredman
*Attorney, Agent, or Firm*—Suiter & Associates PC

[57] ABSTRACT

The invention provides a method for detecting the presence of *Serpulina hyodysenteriae* in a biological sample, an oligonucleotide primer and an *S. hyodysenteriae*-specific oligonucleotide probe useful in that method, and an article of manufacture that contains the primers and/or probe. Also provided are an about 2.3-kb DNA fragment derived from genomic DNA of *S. hyodysenteriae* and encoding for an about 56 kDa polypeptide, a recombinant expression vector containing the DNA fragment, the 56 kDa polypeptide and a monoclonal antibody reactive with the peptide, and a method of assaying for antibodies reactive with the 56 kDa peptide.

22 Claims, 6 Drawing Sheets

OTHER PUBLICATIONS

Jensen et al., "Detection and Identification of *Treponema hyodysenteriae* by Using Oligodeoxynucleotide Probes Complementary to 16S rRNA". *J. Clin. Microbiol.*, 28:2717–2721 (1990) is cited in the specification at p. 5, lines 17–18.

Jones et al., *J. Clin. Microbiol.*, 24:1071–1074 (1986) is cited in the specification at p. 45, lines 19–20.

Judd et al., *Appl. Env. Microbiol.*, 59:1702 (1993) is cited in the specification at p. 28, lines 25–26.

Katz et al., "Colorimetric Diagnosis of Prolonged Bluetongue Viremia in Sheep, Using an Enzyme–linked Oligonucleotide Sorbent Assay of Amplified Viral Nucleic Acids", *Am. J. Vet. Res.*, 54:2021–2026 (1993) is cited in the specification at p. 28, line 23 and p. 32, line 4.

Kinyon and Harris, *Infect. Immun.*, 15:638–646 (1977) is cited in the specification at p. 4, line 3 and p. 44, lines 24–25.

Kohler and Milstein, *Nature* 256:496–97 (1975) is cited in the specification at p. 39, line 3.

Koopman et al., "Cloning and DNA Sequence Analysis of a Serpulina (Treponema) hyodysenteriae Gene Encoding a Periplasic Flagellar Sheath Protein", *Infect. Imm.*, 60:2920–2925 (1992) is cited in the specification at p. 51, line 9–10.

Kunkle et al., *J. Clin. Microbiol.*, 24:669–671 (1986) is cited in the specification at p. 46, line 25 and p. 47, lines 22–23.

Kunkle et al., *J. Clin. Microbiol.*, 24:669–671 (1986) is cited in the specification at p. 3, line 13 and p. 59, line 31.

Kunkle et al., *J. Clin. Microbiol.*, 26:2357–2360 (1988) is cited in the specification at p. 3, line 13 and p. 59, line 31.

Lee et al., *Vet. Microbiol.*, 34:35–46 (1993) is cited in the specification at p. 45, line 13.

Lemcke and Burrows, *Vet. Rec.*, 104:548–551 (1979) is cited in the specification at p. 4, lines 13–14.

Li et al, *J. Clin. Microbiol.*, 29:2794–2797 (1991) is cited in the specificition at p. 2, line 5 and p. 44, line 35.

Lory, *J. Bacteriol.*, 174:3423–3428 (1992) is cited in the specification at p. 50, lines 31–32.

Luneberg et al., "Detection of *Mycoplasma pneumoniae* by Polymerase Chain Reaction and Nonradioactive Hybridization in Microtiter Plates" *J. Clin. Micro.* 31: 1088–1094 (1993) is cited in the specification at p. 28, line 22.

"Reaction and Nonradioactive Hybridization in Microtiter Plates", *J. Clin. Micro.* 31:1088–1094 (1993) is cited in the specification at p. 28, line 22.

Lymbery et al., *Vet. Microbiol.*, 22:89–99 (1990 is cited in the specification at p. 4, line 4.

Lysons, *Vet. Rec.*, 129:314–315 (1991) is cited in the specification at p. 4, lines 19 and 28.

Mapother and Joens, *J. Clin. Micro.*, 22:161–164 (1985) as cited in the specification at p. 2, line 4.

Mowat et al., *Immunology Today*, 12:383 (1991) is cited in the specification at p. 35, line 37.

Muir et al., "Cloning and Expression of a Serpula (Treponema) hypayseneriae Hemolysin Gene", *Infect. Immun.*, 60:529–535 (1992) is cited in the specification at p. 51, lines 5–6.

Mullis and Faloona, *Methods Enzymol.* 155:335 (1987) is cited in the specification at p. 27, line 14.

Owen, *Iowa State J. Res.*, 62:293–311 (1987) is cited in the specification at p. 1, lines 31–32.

Picard et al., *Can. J. Microbiol.*, 26:985–991 (1980) is cited in the specification at p. 4, lines 4–5.

Ramanathan et al., "Identification and Partial Characterization of a Group of Weakly β–hemolytic Intestinal Spirochetes of Swine Distinct from *Serpulina innocens* Isolate", *Vet. Microbiol.*, 37:53–64 (1993) is cited in the specification at p. 4, lines 5–6, p. 45, line 14; p. 47, lines 4–5; and page 54, line 17.

Rychlik and Rhoades, *Nucleic Acid Res.*, 17:8543–8551 (1989) is cited in the specification at p. 55, lines 24–27.

Saiki et al., *Science* 239:487 (1988) is cited in the specification at p. 27, lines 19–20.

Sellwood et al., "Outer Envelope and Axial Filiment Polypeptides of T. hydrodysenteriae, Characterization and Molecular Cloning", *Proc. Inter. Pig. Vet. Soc.*, at p. 119 (1990).

Sellwood, *Proc. 12th Cong. Int. Pig Vet. Soc.*, The Hague, The Netherlands, at p. 264 (1992) is cited in the specification at p. 4, lines 32–33.

Smith et al., *Vet. Microbiol.*, 24:29–41 (1990) is cited in the specification at p. 3, lines 30–31.

Songer and Harris, *Am. J. Vet. Res.*, 39:913–916 (1978) is cited in the specification at p. 2, line 26.

Sotiropoulos et al., *J. Clin. Microbiol.*, 31:1746–1752 (1993) is cited in the specification at p. 5, line 27.

Sotiropoulos et al., *J. Clin. Microbiol.*, 32:1397–1401 (1994) is cited in the specification at p. 5, lines 28–29.

Southern et al., *J. Mol. Biol.*, 98:503–517 (1975) is cited in the specification at p. 53, lines 27–28.

Stanton et al., *Vet Microbiol.*, 18:177–190 (1988) as cited in the specification at p, 46, lines 27–28.

Stanton et al., "Reclassification of *Treponema hyodysenteriae* and *Treponema innocens* in a New Genus, Serpula gen. nov., as *Serpula hyodysenteriae*, comb. nov. and *Serpula innocens* comb. nov.", *Int. J. Syst. Bacteriol.*, 41:50–58 (1991) is cited in the specification at p. 1, lines 36–37.

Taylor et al., *Proc. 12th Congr. Int. Pig Vet. Soc.*, The Hague, The Netherlands, at p. 280 (1992) is cited in the specification at p. 5, lines 3–4.

ter Huurne, "Swine Dysentery Pathogenesis and Vaccine Development", Ph.D. Dissertation, University of Ulbrecht, Nov. 1993 is cited in the specification at p. 51, lines 6–8.

Thomas and Sellwood, *J. Med. Microbiol.*, 37:214–220 (1992) as cited in the specification at p. 4, lines 33–34.

Torp and Thorensen, *Proc. 12th Cong. Int. Pig Vet. Soc.*, The Hague, The Netherlands, at p. 270 (1992) is cited in the specification at p. 4, lines 6–8 and p. 5, line 23.

Welsh et al., "Fingerprinting Genomes Using PCR with Arbitrary Primers", *Nucleic Acids Res.*, 18:7213–7218 (1990) is cited in the specification at p. 28, line 19.

Duhamel et al., "Serodiagnosis of Swine Dysentery Using Recombinant Proteins from *Treponema Hyodysenteriae*", *Nebraska Veterinary Science Newsletter*, 19:3–4.

Duhamel et al., "Update on Prevention and Control of Swine Dysentery", *31st George A. Young Swine Conference and Annual Nebraska SPF Swine Conference*, Lincoln, NE, at pp. 7–20, Aug. 13–14 (1990).

Duhamel et al., "Freedom From Dysentery", *Swine Practitioner*, at pp. 4–5, 8 and 10, Sep. 1990.

Duhamel et al., "Application to Restriction Length Fragment Length Polymorphism Typing to Epidemological Tracing of *Serpulina* (Treponema) *hyodysenteriae*", *Proc. 12th Int. Cong. Pig. Vet. Soc.*, The Hague, Netherlands, vol 1, p. 276 (1992).

Duhamel et al., *J. Vet. Diagn. Invest.*, 4:285–292 (1992) is cited in the specification at p. 58, line 35 and p. 63, line 33.

Duhamel et al., "Herd Health: Swine Dysentery Probe, Promising Cleanup Tool", *National Hog Farmer* at p. 48–50, Dec. 15 (1993).
Elder et al., "Rapid Identification of *Serpulina hyodysenteriae* By Polymerase Chain Reaction", 53rd Annual North Central Branch Meeting, American Society for Microbiology, Oct. 28–30, at p. 21 (1993).
Kunkle et al., "Recombinant DNA Technology in Controlling Swine Dysentery", 1992 *Nebraska Swine Report* at p. 3–4 (1992).
Schafer et al., "Rapid Identification of *Serpulina hyodysenteriae* By Polymerase Chain Reaction Amplification of a DNA Sequecne Unique to *Serpulina hydodysenteriae"*, 32nd North Central Conference Veterinary Laboratory Diagnosticians, Madison, WI, Jun. 8–9 (1993).
Adachi et al., *Zentralbl. Bakteriol.,* 245:527 (1979).
D. Baum et al., *Infect. Immun.,* 25:792 (1979).
"New Swine Dysentery Vaccines May be Just Around the Corner", *Swine Practioner* at pp. 4–6, Jan. (1994).
Chatfield et al., "Identification of the Major Antigens of *Treponema hyodysenteriae* and Comparison with Those of *Treponema innocens", Inf. & Immun.,* 56:1070–1075 (1988).
Fisher et al., "Development and Evaluation of a Whole Cell ELISA for Detection of Serum Antibodies to *Treponema hyodysenteriae* in Swine", Abstract No. 70, 71th Conference of Research Workers in Animal Disease, Nov. 5–6 (1990).
Gabe et al., "Molecular Analysis of the vspA–H Genes Which Comprise a Multigene Family Encoding a 39–kDa Variable Surface Protein from *Sepulina hyodysenteriae",* Abstract D156, 94th ASM General Meeting May 23–27 (1994).
Hampson et al., *Epidemiol. Infect.,* 103:275 (1989).
Hornich et al., in *Vet. Med.,* 24:29 (1979).
Jenkins et al., *Vet Immunological Immunopathology,* 2:19 (1981).
Jenkins, *Am. J. Vet. Res.,* 41:338 (1980).
Jenkins et al., *Brit Vet Journal,* 145:565 (1989).
Joens et al., *Vet. Records,* 106.:245 (1980).
Joens et al., "Molecular Characterization of Proteins from Porcine Spirochetes", *Infect. Imm.,* 54:893–896 (1986).
Kent et al., *J. Gen. Micro.,* 135:1625 (1989).
Lemcke et al., *J. Hygiene,* 86:173 (1981).
Norby, "Veterinary Scientists Hope to Break Swine Dysentery Transmission Cycle", *Research Nebraska!* at pp. 16–17, Sep. (1993).
Quaife, "A New Weapon Against Swine Dysentery", *Swine Practioner* at pp. 10–11, Oct. 1990.
Schlink et al., *Can. J. Comp. Med.,* 47:320 (1983).
Stanton et al., "Proposal to Change the Genus Designation Serpula to Serpulina gen. nov. Containing the Species *Serpulina hyodysenteriae* comb. nov. and *Serpulina innocens* comb. nov.", *Int. J. Syst. Bacteriol.,* 42:189–190 (1992).
Warnemuehler et al., *Infec. Immun.,* 56:3032–3039 (1988).
Williams et al., *Nucleic Acid. Res.,* 18:6531 (1990).
Wright et al., *J. Clin. Micro.,* 27:411–416 (1989).
Bej et al, (1991), "Amplification of nucleic acids by polymerase chain reaction (PCR) and other methods and their applications", Critic. Rev. Biochem. Mol. Biol. 26(3/4):301–334.
Sommer et al, (1989), "Minimal homology requirements for PCR primers", Nuclei Acids Res. 17(16):6749.
Matthews et al, (1988), "Analytical strategies for the use of DNA probes", Anal. Biochem. 169:125.
Dettori et al, (1992), "Molecular cloning and characterization of DNA from human intestinal spirochetes", Europ. J. Epidemiol. 8(2):198–205.
Elder, et al., "Rapid Identification of *Serpulina hyodysentefiae* In Diagnostic Specimens Using Polymerase Chain Reaction", 74th Conference of Research Workers in Animal Disease, Nov. 8–9 (1993).
"Swine Dysentery Products", in *Annual Guide to Herd Health: Pork 94* at pp. 54–55 (1994).

```
CGGCCAGTGC CAAGCTTTAC CAGTTGAGGG CGACTATTAT TCTGATAAAA AAATGTTAAG    60
AAGATTAGAC CCTTTTATTA ATTTTGGAAT ATATGCCGCT CATCATGCAT TTAAGCAGGC   120
TGGTATAGAA CCGAAAACAG GCTTTGATCC TTTAAGAGCC GGTTGTGTTC TTGGTAGCGG   180
TATTGGCGGT ATGACTACTC TTTTATCTAA CCATCAAGTT TTACTTAATG ACGGACCTGG   240
CAGAGTATCA CCTTTCTTTG TACCTATGCA AATAATCAAT ATGACACCTG GTTTAATATC   300
TATGGAATAT GGTATGAACG GACCTAACTA CAGTACAGTT ACTGCATGTG CTTCTTCAAA   360
CCACTCTATA GGTTTAGGTT ATAAACATAT TAAAGATAAT GAAGCTGATA TT ATG       415
                                                          Met
                                                           1

GTA GTT GGA GGT TCT GAA GCT ACT ATA AAT CCT CTT ACT ATA GCT GGT    463
Val Val Gly Gly Ser Glu Ala Thr Ile Asn Pro Leu Thr Ile Ala Gly
              5                  10                  15

TTC AAT AAT GCT AGA GCT TTA TCT ACT AGA AAT GAT GAT CCT GCT AAA    511
Phe Asn Asn Ala Arg Ala Leu Ser Thr Arg Asn Asp Asp Pro Ala Lys
             20                  25                  30

GCA TCA AGA CCT TTT GAT AAA GGA AGA GAC GGA CTT GCT ATA GCC AGA    559
Ala Ser Arg Pro Phe Asp Lys Gly Arg Asp Gly Leu Ala Ile Ala Arg
     35                  40                  45

TAT TTA ATA AAA AAT GGC TAT GAT GTA AAA ATA TAT ATC ACA GGA AAT    607
Tyr Leu Ile Lys Asn Gly Tyr Asp Val Lys Ile Tyr Ile Thr Gly Asn
 50                  55                  60                  65

CTT GAC AGA GTT AAT AAA GAT ACC TAC TCT AAC TTT AAT ATA TTA AAA    655
Leu Asp Arg Val Asn Lys Asp Thr Tyr Ser Asn Phe Asn Ile Leu Lys
                 70                  75                  80

TCT ATG AAT ATA GAT ATT AAT TAT TTA GGA AGC GAA GAA GAT GCC ATA    703
Ser Met Asn Ile Asp Ile Asn Tyr Leu Gly Ser Glu Glu Asp Ala Ile
             85                  90                  95

TCA GCT GCA GAA AAT ATA GAA AGA AAA TCA ATA GTA TTA GAT TCA TTA    751
Ser Ala Ala Glu Asn Ile Glu Arg Lys Ser Ile Val Leu Asp Ser Leu
        100                 105                 110

TTT GGT ACA GGC GGA AAC AGA CCT TTA GAA GGA ATA CAA AAA GCT CTT    799
Phe Gly Thr Gly Gly Asn Arg Pro Leu Glu Gly Ile Gln Lys Ala Leu
    115                 120                 125

ATA GAT AGT TTG AAT AAA TTA GAT GTT CTT AGA ATA GCA ATA GAT ATA    847
Ile Asp Ser Leu Asn Lys Leu Asp Val Leu Arg Ile Ala Ile Asp Ile
130                 135                 140                 145
```

FIG. 1A

```
CCT TCA GGA TTA GCT TCA AAA ATA AAT GAT AAT GAC AAT GTA TAT ACT       895
Pro Ser Gly Leu Ala Ser Lys Ile Asn Asp Asn Asp Asn Val Tyr Thr
                150                 150                 160

TGT TTT AAA GCA CAT GAA ACA TAT ACT ATA TGC TTC GCT AAA GAT ATA       943
Cys Phe Lys Ala His Glu Thr Tyr Thr Ile Cys Phe Ala Lys Asp Ile
            165                 170                 175

TTC TTT TTA TAC AGA ACA AGA GAA TAT ATA GGA AAA TTA TTC ATA ATA       991
Phe Phe Leu Tyr Arg Thr Arg Glu Tyr Ile Gly Lys Leu Phe Ile Ile
        180                 185                 190

AAA TCA ATA TTC CCA GAT GAA ATA TTA GAT AAT TGG GGA TAT AAA GCT      1039
Lys Ser Ile Phe Pro Asp Glu Ile Leu Asp Asn Trp Gly Tyr Lys Ala
    195                 200                 205

AAA CTT ATA GAT TAT AAT GAA AAA ATA AAT ATA AAT AGA AAC TCT CTA      1087
Lys Leu ile Asp Tyr Asn Glu Lys Ile Asn Ile Asn Arg Asn Ser Leu
210                 215                 220                 225

TAC AGC AAA AGA GAA CAA GGA ATG CTT GCT ATA GTA GCA GGA AGT GAT      1135
Tyr Ser Lys Arg Glu Gln Gly Met Leu Ala Ile Val Ala Gly Ser Asp
                230                 235                 240

AAT TAT ATA GGG GCT GCT GTT CTA GCT GTA AAT GCT GCT TAT AGA TTG      1183
Asn Tyr Ile Gly Ala Ala Val Leu Ala Val Asn Ala Ala Tyr Arg Leu
            245                 250                 255

GGT GTA GGA TAC ATA AGA TTA TAT GTA CCT AAA GGC ATA ATA AAA AAT      1231
Gly Val Gly Tyr Ile Arg Leu Tyr Val Pro Lys Gly Ile Ile Lys Asn
        260                 265                 270

ATA AGA GAT GCC ATA ATG CCT TCT ATG CCT GAA ATT GTT ATT ATA GGA      1279
Ile Arg Asp Ala Ile Met Pro Ser Met Pro Glu Ile Val Ile Ile Gly
    275                 280                 285

GTT GGA GAA GAA AAT CAA AAA TTC TTC ACA GAA AAT GAC ATT GAA ATA      1327
Val Gly Glu Glu Asn Gln Lys Phe Phe Thr Glu Asn Asp Ile Glu Ile
290                 295                 300                 305

GTA AAT GAT ATT AAT AAA AGC GAT GCT TGT ATA ATA GGT TCT GGT ATA      1375
Val Asn Asp Ile Asn Lys Ser Asp Ala Cys Ile Ile Gly Ser Gly Ile
                310                 315                 320

GGC AGA GAT TTG TCT ACA GAA ATT TTT GTA AAT ACT ATA TTA AAG CAA      1423
Gly Arg Asp Leu Ser Thr Glu Ile Phe Val Asn Thr Ile Leu Lys Gln
            325                 330                 335

ATA AAT ATA CCT ACT GTT ATT GAT GCT GAT GCT TTA TAT TTA ATG TTT      1471
Ile Asn Ile Pro Thr Val Ile Asp Ala Asp Ala Leu Tyr Leu Met Phe
        340                 345                 350
```

FIG. 1B

GAA AGC ACT CTT AAT GAA CTT AAT AAT AAT TTT ATA ATC ACT CCT CAT 1519
Glu Ser Thr Leu Asn Glu Leu Asn Asn Asn Phe Ile Ile Thr Pro His
355 360 365

ATA TAT GAA TTT GAA AAA CTT ACA CAG ATA AAT CAT ATA GAG GTT TTA 1567
Ile Tyr Glu Phe Glu Lys Leu Thr Gln Ile Asn His Ile Glu Val Leu
370 375 380 385

GAA AAT CCT TAT CAG GCA TTA TTA ATA TAC AGA GAA AAA ACT AAT GCC 1615
Glu Asn Pro Tyr Gln Ala Leu Leu Ile Tyr Arg Glu Lys Thr Asn Ala
390 395 400

TCA ATA GTA TTA AAA GAT GCT GTA AGT TTC CTA ATG CAT GAA AAT GAT 1663
Ser Ile Val Leu Lys Asp Ala Val Ser Phe Leu Met His Glu Asn Asp
405 410 415

ATA TAT ATA AAT TAT AAC CCT AGA GAA TCT ATG GGG AAA GCA GGT ATG 1711
Ile Tyr Ile Asn Tyr Asn Pro Arg Glu Ser Met Gly Lys Ala Gly Met
420 425 430

GGT GAT GTT TTT GCT GGA TTT ATA GGT GCT TTG CTC GCT AGA AAA CTA 1759
Gly Asp Val Phe Ala Gly Phe Ile Gly Ala Leu Leu Ala Arg Lys Leu
435 440 445

AAT ATA TTA GAT GCT TCA AAA CTA GCA TTG ATA ATA CAG GCT AAA TCT 1807
Asn Ile Leu Asp Ala Ser Lys Leu Ala Leu Ile Ile Gln Ala Lys Ser
450 455 460 465

TTT AAT ATA TTA TCA AAA AAA TTC GGA AAT GAT TAT ATT CAG CCT AAA 1855
Phe Asn Ile Leu Ser Lys Lys Phe Gly Asn Asp Tyr Ile Gln Pro Lys
470 475 480

GAT TTG GCA AAT ATT TCA TAT AAA ATA CTA AAA GGA TAT AAA TTT GCC 1903
Asp Leu Ala Asn Ile Ser Tyr Lys Ile Leu Lys Gly Tyr Lys Phe Ala
485 490 495

TAGAGAAGTT TACGACCCTA AACAAAAAGA ATTAGAATTC TACGCTAAAA GAGAGGTAAA 1963

GCCCCCTGCT CCTAAAAGAG AGGTAAGCAT ATTTGCTAGA AGATGGTTTA TGTTTTTATA 2023

CGGAACTTTC CTCACATTAG TTGTAATTGG TATGCTTTTA TATAAAAAAG GATTCTTTAA 2083

TAATATACCA TTATTTGAAG CTTTAAAGCC TAAAACAGAT GTTATAGTAA AAATTAATAA 2143

TGCTGAATTC GTTAATGATG CAGTAATTAC AACTATAGAA CTCGAAAATT CAAATTATAC 2203

TAATTCTGAA AGTATAGAAA CACTAAGAAG TTATTTTTCA TTGTACAAAA ATAGAAAATT 2263

AATATTTACA GGCAATCGTT CTTTTAATAA TATAAGATTC CCAGTAGGTC AGAGAATAGG 2323

ATTCAATTT 2332

FIG. 1C

NUCLEOTIDE SEQUENCES AND METHODS FOR DETECTION OF *SERPULINA HYODYSENTERIAE*

STATEMENT REGARDING FEDERALLY SPONSORED RESEARCH

The invention described herein was made with the assistance of funds provided by the U.S. Department of Agriculture/CSRS, Animal Health Project No. Neb. 14-048, Immunobiology of Enteric Diseases of Swine and Cattle; U.S. Department of Agriculture, Regional Research Project NC-62, Prevention of Enteric Diseases of Swine; U.S. Department of Agriculture/NC-IPM, No. Neb. 14-062, Integrated Management Practices for Control of Swine Dysentery and Salmonellosis. The Government has certain rights in the invention.

BACKGROUND OF THE INVENTION

Swine dysentery is a highly contagious disease of growing and finishing swine which has a significant economic impact on the United States swine industry. Although the causative agent has been known for nearly 20 years, no effective measures, other than medication of animals and sanitation of premises, are available to prevent the occurrence of the disease or reduce its severity once introduced into a susceptible herd. Recently published data from Iowa State University indicated a projected statewide cost for prevention and control of swine dysentery of approximately $2.4 million per month. Since the Iowa swine population represents one-fourth of the nation's industry, the annual losses due to swine dysentery for the United States may represent as much as $115.2 million. Owen, *Iowa State J. Res.*, 62:293–311 (1987).

*Serpulina hyodysenteriae* is the primary etiologic agent of swine dysentery. Harris and Lysons, *Diseases of Swine*, 7th ed., Iowa State University Press (Ames, Iowa), at pp. 599–616 (1992); and Stanton et al., *Int. J. Syst. Bacteriol.*, 41:50–58 (1991). Nine serotypes of *S. hyodysenteriae* have been recognized worldwide, with serotypes 1 and 2 being the most prevalent in the United States. Baum and Joens, *Infect. Immun.*, 25:792–796 (1979); Mapother and Joens, *J. Clin. Micro.*, 22:161–164 (1985); and Li et al., *J. Clin. Microbiol.*, 29:2794–2797 (1991). The diagnosis of swine dysentery is based on herd history, clinical signs, observation of characteristic intestinal lesions, and isolation of *S. hyodysenteriae* from feces or intestine using selective agar medium incubated anaerobically for 2 to 4 days. Chengappa et al., *Report of the Committee on Swine Dysentery*, American Association of Veterinary Laboratory Diagnosticians, Inc. (Columbia, Mo.) (1989). Laboratory confirmation of *S. hyodysenteriae* by culture is based upon colony morphology, pattern and intensity of hemolysis, and other growth characteristics, all of which are very similar for the non-pathogenic *Serpulina innocens*, a common inhabitant of the colon of swine. Kinyon and Joens, (1979). As a result, a definitive diagnosis of swine dysentery can be very challenging particularly when the disease occurs on premises where weakly β-hemolytic intestinal spirochetes (WBHIS) are present in the swine population.

An important aspect of swine dysentery is the occurrence of prolonged shedding of *S. hyodysenteriae* in the feces of some animals following recovery from diarrhea. Songer and Harris, *Am. J. Vet. Res.*, 39:913–916 (1978); and Fisher and Olander, *Am. J. Vet. Res.*, 46:450–455 (1981). Asymptomatic carrier-shedder swine are important reservoirs for maintenance of *S. hyodysenteriae* on infected premises and transmission of the organism to uninfected premises. The solution to swine dysentery prevention lies in being able to quickly and accurately identify carrier-shedder swine and avoid their entry into uninfected herds. However, identification of asymptomatic carrier-shedders of *S. hyodysenteriae*, is difficult due to the detection limits of currently available laboratory isolation procedures.

Direct culture of diagnostic specimens is the only method available for laboratory identification of *S. hyodysenteriae*. However, it is well known that the sensitivity of the direct culture method depends upon the number of organisms present in the sample, which in turn depends on the stage of infection of the animal at the time of collection. Kunkle and Kinyon reported that the numbers of *S. hyodysenteriae* in porcine colonic contents at the onset of swine dysentery ranged between $2\times10^6$ and $2\times10^{10}$ CFU/g when cultured using the selective BJ medium. Kunkle et al., *J. Clin. Microbiol.*, 26:2357–2360 (1988). In contrast, subclinically affected animals may shed recoverable numbers of spirochetes only sporadically and in much lower numbers than animals with clinical swine dysentery often resulting in false negative culture results. Field cases of swine dysentery also may contain drug residues that adversely affect recovery of viable *S. hyodysenteriae* by culture.

Identification of *S. hyodysenteriae* by culture is highly subjective and can lead to false results, particularly when results of cultures are interpreted by inexperienced laboratory workers. For this reason, several biochemical tests have been proposed for rapid differentiation of enteropathogenic and non-pathogenic intestinal spirochetes of swine. Achacha et al., *J. Vet. Diag. Invest.*, 3:211–214 (1991); Belanger et al., *J. Clin. Microbiol.*, 29:1727–1729 (1991); Hunter et al., *Vet. Rec.*, 104:383–384 (1979); and Smith et al., *Vet. Microbiol.*, 24:29–41 (1990). Although these biochemical characteristics are highly conserved among field isolates of *S. hyodysenteriae*, WBHIS have been shown to yield highly variable results making a conclusive identification of *S. hyodysenteriae* based on biochemical tests alone practically impossible. Achacha et al, cited supra; Belanger et al., cited supra; Burrows et al., *Vet. Rec.*, 108:187–189 (1981); Kinyon et al., *Infect. Immun.*, 15:638–646 (1977); Lymbery et al., *Vet. Microbiol.*, 22:89–99 (1990); Picard et al., *Can. J. Microbiol.*, 26:985–991 (1980); Ramanathan et al., *Vet. Microbiol.*, 37:53–64 (1993); and Torp and Thorensen, *Proc. 12th Congr. Int. Pig Vet. Soc.*, The Hague, The Netherlands, at page 270. (1992). In addition, the biochemical tests require growth of the organism for 2 to 4 days.

Other methods of differentiating *S. hyodysenteriae* from WBHIS include growth inhibition by discs soaked in antiserum (Lemcke and Burrows, *Vet. Rec.*, 104:548–551 (1979)) and rapid slide agglutination (Burrows and Lemcke, *Vet. Rec.*, 108:187–189 (1981)). In addition to problems of non-specific clumping of spirochetes in the saline control in the slide agglutination test, these tests require large numbers of pure culture of spirochetes which can take up to 3 weeks to grow. Lysons, *Vet. Rec.*, 129:314–315 (1991). Although pre-absorption of reference polyclonal antisera with WBHIS increases the specificity of the serological tests, occasional *S. hyodysenteriae* isolates continue to be falsely classified as non-pathogenic in these tests. An alternative method using microscopic agglutination under phase contrast or dark field microscopy was recently proposed. However, some isolates of *S. hyodysenteriae* gave weaker reactions in that assay than with the slide agglutination test (Lysons, cited supra).

Mouse monoclonal antibodies capable of differentiating *S. hyodysenteriae* from porcine WBHIS have also been proposed as potential diagnostic reagents. Sellwood et al.,

*Proc. 12th Congr. Int. Pig Vet. Soc.*, The Hague, The Netherlands, at page 264 (1992); and Thomas and Sellwood, *J. Med. Microbiol.*, 37:214–220 (1992). However, other studies indicate that spirochetes other than *S. hyodysenteriae* can express antigenic determinants recognized by these reagents and cause false positive results. Taylor et al., *Proc. 12th Congr. Int. Pig Vet. Soc.*, The Hague, The Netherlands, at page 280 (1992). The fact that no serological reagents are available commercially also limits the applicability of serological techniques to routine diagnosis of swine dysentery.

Certain genes encoding *S. hyodysenteriae* antigens and capable of eliciting protection against infection in mice have been cloned and expressed in *Escherichia coli* using a phage expression system. Boyden et al., *Infect. Immun.*, 57:3808–3815 (1989). However, none of these reagents has been examined for potential application as diagnostic tools. One of the most recent diagnostic applications of recombinant DNA technology to swine dysentery control used oligodeoxynucleotide probes to 16S rRNA of *S. hyodysenteriae*. Jensen et al., *J. Clin. Microbiol.*, 28:2717–2721 (1990). However, the sensitivity of this probe method for detection of spirochetes in feces was equivalent to routine bacteriological culture ($10^5$ organisms/g of feces), and further studies question the specificity of the 16S rRNA probe to *S. hyodysenteriae* (Torp and Thoresen, cited supra). Dot blot hybridization with whole-chromosomal probes and DNA probes for identification of *S. hyodysenteriae* have been reported. Combs and Hampson, *Res. Vet. Sci.*, 50:286–289 (1991); Sotiropoulos et al., *J. Clin. Microbiol.*, 31:1746–1752 (1993); and Sotiropoulos et al., *J. Clin. Microbiol.*, 32:1397–1401 (1994). Although the sensitivity of the whole-chromosomal probes was not reported, colony dot blot hybridization with DNA probes was shown to be only slightly better than culture ($10^4$ organisms/g of feces). These tests are labor intensive, require specialized equipment, and have turn-around times that are incompatible with routine laboratory diagnosis.

A solution to prevention of disease caused by *S. hyodysenteriae* lies in being able to quickly and accurately identify carrier-shedder animals and avoid their entry into uninfected herds. Therefore, there is a need to develop a method and reagents for detecting *S. hyodysenteriae* in low numbers specifically, rapidly and directly from diagnostic and environmental samples. There is also a need to develop a sensitive and specific method for rapid detection of *S. hyodysenteriae* in a biological sample to diagnose and monitor infection in acutely- or subclinically-infected animals before, during and after treatment and in their environment. There is also a need to develop a method for rapid detection of *S. hyodysenteriae* for monitoring disinfection of the environment in contact with infected animals.

SUMMARY OF THE INVENTION

These and other objects are achieved by the present invention which is directed to a method for detecting the presence of at least one serotype of *Serpulina hyodysenteriae* in a biological sample, an oligonucleotide primer, and a *S. hyodysenteriae*-specific oligonucleotide probe useful in that method, and an article of manufacture (i.e., kit) containing the primers and/or probe. Also provided are an about 2.3-kb DNA fragment derived from chromosomal DNA of *S. hyodysenteriae* B204 serotype 2 that encodes for an about 56 kDa polypeptide, a recombinant expression vector containing the DNA fragment, the about 56 kDa polypeptide and a monoclonal antibody reactive with the peptide. The invention also provides for a method of immunizing animals and vaccine preparations for protecting animals against disease caused by *S. hyodysenteriae*. The methods and compositions of the invention are useful to identify at least one serotype of *S. hyodysenteriae*, to diagnose *S. hyodysenteriae* infection, to detect carrier-shedder animals, to monitor efficacy of treatment for disease caused by *S. hyodysenteriae*, to monitor disinfection of fomites, and to protect animals from infection with *S. hyodysenteriae*.

According to the invention, a biological sample of an animal such as feces, intestinal contents, mucosal scrapings, rectal swabs, and environmental samples among others, is tested for the presence of at least one serotype of *S. hyodysenteriae* by measuring the presence or absence of DNA amplification products from a primer that hybridizes to a 2.3 kb HindIII restriction fragment of *S. hyodysenteriae* B204 serotype 2. The 2.3 kb HindIII restriction fragment was obtained from a partial digest with HindIII and preferably has a nucleotide sequence as shown in FIG. 1 (SEQ ID NO:1). The DNA amplification products specific for *S. hyodysenteriae* can be detected by (a) extracting DNA from a biological sample; (b) amplifying a target sequence of the extracted DNA to provide DNA amplification products carrying a selected target DNA sequence; and (c) detecting the presence of *S. hyodysenteriae* by detecting the presence of the DNA amplification products. Preferably, the amplification of the DNA sequence is by polymerase chain reaction (PCR) by amplifying the gene sequence with DNA polymerase and at least one oligonucleotide primer. The primers preferably have a sequence of positive-sense 5'-GGTACAGGCGGAAACAGACCTT (SEQ ID NO:3) corresponding with nucleoitdes 757-718 of SEQ ID NO: 1, or negative-sense 5'-TCCTATTCTCTGACCTACTG (SEQ ID NO:4) corresponding with nucleotides 2288-2300 of SEQ ID NO:1, or complements thereof or mixtures thereof.

The amplification products can be detected, for example, by dot blot or Southern blot analysis including by reacting the DNA amplification products with a labeled oligonucleotide probe that can hybridize to the about 2.3 kb HindIII DNA fragment of *S. hyodysenteriae* B204 serotype 2 shown in FIG. 1. Prior to detection, the DNA amplification products can optionally be separated by electrophoresis. Alternatively, the PCR products can be detected by immobilization to a bead or a multiwell plate by a probe or primer labeled with biotin, followed by hybridization with a detectably labeled probe. The oligonucleotide probe preferably hybridizes to all or a portion of a 2.3 kb HindIII DNA fragment of *S. hyodysenteriae* B204 serotype 2 having the nucleotide sequence shown in FIG. 1 (SEQ ID NO:1). The detection of amplified products preferably allows for the detection of all serotypes of *S. hyodysenteriae* at low levels of bacteria in the sample (i.e., about 1 to 10 microorganisms/0.1 gm sample).

The invention provides an isolated HindIII DNA fragment of about 2.3-kb that is derived from a partial digest of chromosomal DNA of *S. hyodysenteriae* B204 serotype 2 with HindIII, which encodes for an about 56 kDa polypeptide. The DNA fragment preferably has the nucleotide sequence shown in FIG. 1 (SEQ ID NO:1).

The DNA restriction fragment may be incorporated into an expression vector. The expression vectors include the restriction fragment operably linked to transcriptional and translational control regions in the vector. The expression vectors are useful to form transformed cells. The transformed cells can be used to screen monoclonal antibodies specific for *S. hyodysenteriae* to produce a 56 kDa polypeptide of *S. hyodysenteriae*, to prepare mutant sequences of the 2.3 kb HindIII restriction fragments, and as an intermediate to prepare the 2.3 kb HindIII restriction fragment for DNA sequencing. A pUC18 plasmid carrying the 2.3 kb HindIII restriction fragment from *S. hyodysenteriae* B204 and designated pRED3C6, deposited with the American Type Culture Collection, Rockville, Md., has been given Accession No. 75826.

Also provided are oligonucleotide primers that hybridize to all or a portion of a DNA sequence of the 2.3 kb HindIII fragment of *S. hyodysenteriae* B204 serotype 2 (SEQ ID NO:1). The DNA sequence of an oligonucleotide primer is preferably positive-sense 5'-GGTACAGGCGGAAACAGACCTT (SEQ ID NO:3) and negative-sense 5'-TCCTATTCTCTGACCTACTG (SEQ ID NO:4), or complements thereof or mixtures thereof. The primers can be complementary to the 3' or 5' end of the target sequences. The primers can also have mismatches with the target sequence or be degenerate.

The target DNA sequence is also useful in providing an oligonucleotide probe for detecting a target sequence of at least one serotype of *S. hyodysenteriae*. The probe is preferably hybridizable with a DNA sequence located on the 2.3 kb HindIII fragment of the chromosomal DNA of *S. hyodysenteriae*, preferably a 1.55 kb DNA sequence within the 2.3 kb fragment. The DNA sequence of the oligonucleotide probe is preferably hybridizable to all or a portion of the 2.3 kb HindIII fragment of *S. hyodysenteriae* B204, as shown in FIG. 1, and can distinguish *S. hyodysenteriae* from other microorganisms and cells in a biological sample.

The about 56 kDa polypeptide encoded by the about 2.3 kb DNA fragment is useful in eliciting antibodies that are specifically reactive with *S. hyodysenteriae*. The 56 kDa polypeptide and nucleotide sequence encoding the polypeptide may also be useful in a vaccine preparation to provide a protective effect for an infection caused by *S. hyodysenteriae*. The invention further provides an in vitro assay for detecting *S. hyodysenteriae*-specific antibodies in a sample. In that method, a sample to be tested is contacted with a composition containing the about 56 kDa polypeptide, which is preferably labelled, to form a conjugate which is then detected.

An article of manufacture (i.e., kit) is also provided for use in the detection of at least one serotype of *S. hyodysenteriae* in a biological sample. The kit is composed of one or more reagents contained within a packaging material, the reagents useful for detection of the spirochete including at least one oligonucleotide primer that hybridizes to a DNA sequence of the 2.3 kb fragment of *S. hyodysenteriae* B204 as shown in FIG. 1, and/or an oligonucleotide probe which is hybridizable to all or a portion of a DNA gene sequence included in the 2.3 kb gene fragment, preferably an about 1.55 kb gene fragment. The kit may optionally include instruction means with information regarding the use of the reagent and/or other component of the kit such as how to conduct an assay, and the like. The instruction means may be a label or tag attached to the packaging, a printed package insert, and the like. Two or more reagents and/or other components may be combined together to form the kit, preferably packaged together within containing means such as a box or plastic bag, and the like.

The kits and methods of the invention can be used to identify at least one serotype of *S. hyodysenteriae* to diagnose *S. hyodysenteriae* infection, detect carrier-shedder animals, monitor the efficacy of treatment for diseases caused by *S. hyodysenteriae*, or monitor disinfection of the environment. A method for monitoring the efficacy of treatment is useful to ensure that subclinically infected or carrier-shedder animals are not formed. The method involves monitoring the presence of *S. hyodysenteriae* throughout the course of treatment of the animal. The presence of *S. hyodysenteriae* in a biological sample from the treated animal is detected by detecting DNA amplification products of a target sequence of *S. hyodysenteriae*, wherein the target sequence is a 2.3 kb HindIII restriction fragment of *S. hyodysenteriae*.

The invention also provides for vaccines and methods of immunizing an animal to produce a protective immune response against *S. hyodysenteriae* infection. The vaccines include an amount of a 56 kDa polypeptide encoded on a 2.3 kb HindIII restriction fragment of *S. hyodysenteriae* B204 effective to induce a protective response to *S. hyodysenteriae* infection. The vaccine preparations are in admixture with a physiologically acceptable carrier and can be administered to animals using standard methods. The vaccines and methods of the invention are useful to prevent the adverse effects of disease caused by *S. hyodysenteriae*.

BRIEF DESCRIPTION OF THE DRAWINGS

FIG. 1 shows the nucleotide sequence of the recombinant 2.3-kb HindIII DNA fragment from *Serpulina hyodysenteriae* (SEQ ID NO:1) which indicates a single open reading frame encoding a protein with a predicted molecular weight of approximately 56 kDa (SEQ ID NO:2).

FIG. 4A shows the amplified products electrophoresed on a 0.8% agarose gel and stained with ethidium bromide. FIG. 4B shows hybridization of transferred DNA from the same gel with an internal *S. hyodysenteriae*-specific oligonucleotide probe 5'-end labelled with [γ-$^{32}$P]ATP. Lanes: 1, molecular weight standard (1-kb DNA ladder; GIBCO-BRL); lanes 2 to 9, feces containing $10^5$, $10^4$, $10^3$, $10^2$, $10^1$, $10^0$, $10^{-1}$, $10^{-2}$ *S. hyodysenteriae* cells/0.1 g, respectively.

DETAILED DESCRIPTION OF THE INVENTION

Figure 2:
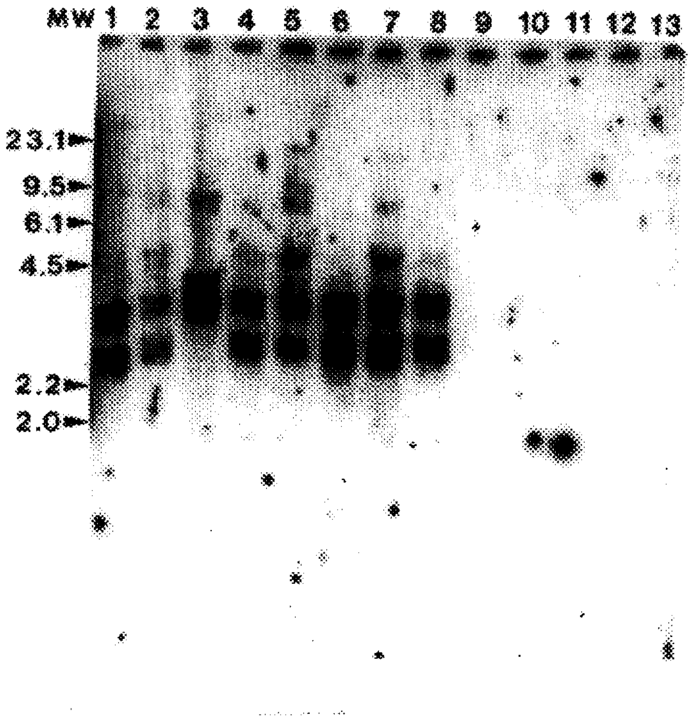
FIG. 2 is a photograph of a Southern blot hybridization using [α-$^{32}$P]dCTP labelled 2.3 kb fragment of clone pRED3C6 to purified chromosomal DNA. Purified chromosomal DNA was digested with HindIII, electrophoresed on a 0.8% agarose gel, and transferred to a nylon membrane. Lanes 1 to 8, *Serpulina hyodysenteriae* isolate B78, B234, B204, B169, A1, B8044, B6933, and AcK 300/8, respectively; lanes 9 to 12, WBHIS B256, B359, B1555a, and 4/71, respectively; lane 13, *Treponema succinifaciens*.

The invention provides for methods, kits and compositions useful for diagnosis and monitoring of infection of animals with at least one serotype of *S. hyodysenteriae*. The compositions include probes and primers that can hybridize to a target sequence of at least one serotype of *S. hyodysenteriae*. The probes and primers can preferably hybridize to all serotypes of *S. hyodysenteriae* and not other closely related microorganisms. The target sequence is preferably about a 2.3 kb fragment of *S. hyodysenteriae* chromosomal DNA having the nucleotide sequence shown in FIG. 1 (SEQ ID NO:1). The primers and probes can be used in methods and kits for detecting *S. hyodysenteriae* in a biological sample, preferably by detecting amplification products using primers that hybridize to the target sequence.

The invention also provides a 56 kDa polypeptide encoded by a 2.3 kb HindIII restriction fragment of *S. hyodysenteriae* B204, as shown in FIG. 1. The polypeptide and nucleotide sequences are useful to elicit antibodies and in vaccine formulations. The vaccine can be administered to animals to induce a protective immune response against infection with *S. hyodysenteriae*.

1. Primers and Probes that Hybridize to a Target Sequence of *S. hyodysenteriae*.

Primers and probes of the invention are useful for identification of at least one serotype of *S. hyodysenteriae* in a biological sample. The primers and probes are preferably those that hybridize to a target sequence of about a 2.3 kb fragment of *S. hyodysenteriae* B204 having the nucleotide sequence of FIG. 1 (SEQ ID NO:1). Hybridization of the primers and/or probes to the target sequence preferably can provide for identification of all serotypes of *S. hyodysenteriae* and distinguish *S. hyodysenteriae* from other cells and closely related microorganisms. Primers can be useful in a diagnostic assay to identify at least one serotype of *S. hyodysenteriae* and to distinguish *S. hyodysenteriae* from at least one other microorganism, and to form probes or to form deletion mutants of the target sequence. Probes are useful to identify at least one serotype of *S. hyodysenteriae* and/or to distinguish *S. hyodysenteriae* from at least one other microorganism, to identify amplification products of a target sequence, and to identify other target sequences.

Primers and probes in accord with the invention are selected so that they can specifically identify at least one serotype of *S. hyodysenteriae*, preferably all serotypes. Those primers or probes that can specifically identify *S. hyodysenteriae* are those that hybridize to a target sequence preferably found in all serotypes and not found in other closely related microorganisms. One such target sequence identified in all serotypes of *S. hyodysenteriae* is about a 2.3 kb fragment of *S. hyodysenteriae* B204 shown in FIG. 1. The 2.3 kb fragment was obtained by partial digestion of chromosomal DNA with HindIII.

The target sequence specific for *S. hyodysenteriae* can be identified from a DNA or cDNA library of *S. hyodysenteriae* chromosomal DNA or mRNA, respectively. A DNA or cDNA library can be generated by standard methods using a restriction enzyme such as HindIII. Suitable host cells such as *E. coli* DH5α and the like are transformed with the library. Transformed cells can be screened by a variety of standard methods including by reactivity with antibodies that react with antigens of *S. hyodysenteriae*.

Once a clone that reacts with the antibodies that react with antigens of *S. hyodysenteriae* is identified, it can be amplified and sequenced. An example of a target sequence is a 2.3 kb fragment having a nucleotide sequence shown in FIG. 1 (SEQ ID NO 1). This sequence encodes a 56 kDa polypeptide having a predicted amino acid sequence as shown in FIG. 1 (SEQ ID NO:2). Transformed cells including this target sequence were immunoreactive with monoclonal antibody 10G6/G10 (available from Dr. Duhamel at University of Nebraska, Lincoln, Nebr.) raised against cell-free supernatant antigens of *S. hyodysenteriae* B204.

A target sequence can be isolated and labeled with a detectable label such as a radioactive nucleotide. The target sequence can also serve as a probe and can be screened for hybridization to all serotypes of *S. hyodysenteriae* and for lack of hybridization to other microorganisms such as *S. innocens*, WBHIS strains, Treponema spp., *E. coli*, Salmonella spp., Campylobacter spp., *Bacteriodis vulgatus*, *Spirocheta aurantia*, *Borrellia burgdorferi*, and Leptospiraceae. Hybridization conditions are preferably low stringency conditions. The target sequence, as well as probes and primers derived from the target sequence, can be used to confirm the identity of a pure culture of *S. hyodysenteriae* isolated by conventional microbiological methods or isolated by immunoaffinity methods and, to distinguish at least one serotype of *S. hyodysenteriae* (in the parts FIG. 1A, 1B, and 1C) from other cells in a mixed biological sample including other microorganisms and eukaryotic cells. Preferably the probe derived from a target sequence can hybridize to all serotypes of *S. hyodysenteriae* and not to closely related *S. innocens*, WBHIS strains, Treponema spp. Once a target sequence is identified, screened for specificity for at least one serotype to *S. hyodysenteriae* and sequenced, it can be used to design primers and/or probes.

Once the sequence of a target sequence from one serotype of *S. hyodysenteriae* is known, primers and probes that hybridize to the known target sequences can be used to identify other closely related target sequence from other serotypes that will hybridize to the same primers and/or probes. For example, other target sequences from other serotypes of *S. hyodysenteriae* can have some DNA sequence differences from the 2.3 kb HindIII restriction fragment from B204 serotype 2, shown in FIG. 1, and still be able to hybridize to primers and probes that hybridize to the 2.3 kb sequence as shown in FIG. 1 under low, medium or high stringency conditions. These other target sequences, once identified, can be sequenced and used to provide a template for design of primers and/or probes. Once selected, these target sequences are further preferably screened for the ability to hybridize to sequences in all serotypes of *S. hyodysenteriae* and not to related microorganisms such as *S. innocens*, Treponema spp., and WBHIS spp., and the like.

At least one primer is designed to be useful to amplify the target DNA sequence preferably using standard or hot start polymerase chain reaction. A primer can preferably be about 16 to 30 nucleotides long and more preferably about 20 to 21 nucleotides long. Primers can hybridize to sequences flanking the desired target sequence which is preferably all or a portion of a 2.3 kb fragment of *S. hyodysenteriae* B204 having the nucleotide sequence shown in FIG. 1. Primers can hybridize to sequences at the 5' and/or 3' ends of the target sequence. Primers can hybridize to the DNA strand with the coding sequence of a target sequence and are designated sense primers. Primers can hybridize to the DNA strand that is the complement of the coding sequence of a target sequence and are designated anti-sense primers. Primers that hybridize to each strand of DNA in the same location or to one another are known as complements of one another. Primers can be designed to hybridize to a mRNA sequence complementary to a target DNA sequence and are useful in reverse transcriptase PCR.

Hybridization conditions utilized are those preferred for polymerase chain reaction modified as required for the degree of sequence complementarity of the primers to the target sequence. Hybridization conditions for a primer of about 16 to 30 nucleotides long having no mismatches with the target sequence are those described by Elders et al., *J. Clin. Micro.*, 32:1497 (1994). Briefly, a PCR mixture including 4 mM $MgCl_2$, 0.2 mM dNTPs and a DNA polymerase are mixed with the DNA extracted from the biological sample. Initial denaturing is at 95° C. for 60 seconds followed by 30 cycles (65° C. for 60 seconds and 72° C. for 120 seconds). The conditions selected are those described for GenAmp 480 (Perkin-Elmer, Norwalk, Conn.).

Hybridization conditions for a primer having about 16 to 30 nucleotides and about up to 30% mismatch are modified as described in Maniatis, *Molecular Cloning: A Laboratory Manual*, Cold Spring Harbor, N.Y. (1989). The melting temperature (TM) for hybridization is decreased about 1° to 1.5° C. for each 1% of mismatch. Primers less than 20 nucleotides preferably only have about one to three mismatches with the target sequence located at either the 5' or 3' end of the primer. PCR methods using mismatched primers or degenerate primers have been described.

Primers can be designed as overlapping sequences or a nested set as long as all or a portion of the target sequence can be amplified. Primers can include at least about 16 nucleotides starting from the flanking sequence immediately adjacent to the 5' end of the target sequence and overlapping primers can be designed to move from the 5' end to the 3' end of the target sequence as shown below:

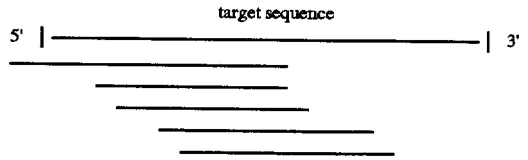

Likewise, primers can be designed to include about 16 nucleotides starting from the flanking sequence immediately adjacent to the 3' end and then overlapping the sequence until the 5' end of the target sequence. These primers can vary in size from about 16 to 100 nucleotides. A primer that hybridizes to a flanking region preferably hybridizes to about 16 to 30 nucleotides immediately upstream or downstream from the target sequence. These overlapping primers provide for amplification of all or a portion of the target sequence preferably at least about 16 nucleotides long and more preferably about 20 to 2,300 nucleotides long.

Primers can preferably hybridize under standard conditions for polymerase chain reaction to a portion of the target nucleotide sequence or to the flanking sequences immediately adjacent to the target sequence and provide for amplification of all or a portion of a target sequence including preferably a 2.3 kb HindIII partial digest restriction fragment of *S. hyodysenteriae* B204. Primers preferably hybridize to the target sequence with no mismatches. However, primers can have additional nucleotide sequence at the 5' or 3' ends, as for example, to provide restriction enzyme recognition sequences. Restriction enzyme recognition sequences are known to those with skill in the art and can provide an amplified product with restriction endonuclease recognition sequence at one or both ends of the amplified products. Other sequences can be added at one or both ends of the primers to act as markers of the amplified products as, for example, a universal primer sequence.

Primers can also be designed that are not perfectly complementary and still can hybridize to a portion of the target sequence or flanking sequence and thereby provide for amplification of all or a portion of a target sequence. Primers of about 20 nucleotides or less preferably have about one to three mismatches located at the 5' and/or 3' ends. Primers of about 20 to 30 nucleotides have up to 30% mismatches and can still hybridize to a target sequence. Hybridization conditions for primers with mismatch can be determined by the method described in Maniatis at pages 11.55 to 11.57 which is hereby incorporated by reference or by reference to known methods. The ability of the primer to hybridize to the 2.3 kb HindIII sequence of FIG. 1 under varying conditions can be determined using this method. Because a target sequence is known, the effect of mismatches can be determined by methods known to those of skill in the art. Hybridization conditions for polymerase chain reaction using degenerate or mismatched primers are known to those of skill in the art.

In a preferred version, primer pairs are designed to flank a desired portion of the target sequence. A primer pair has a first primer that hybridizes to a sense strand at the 5' end of the target sequence and a second primer that hybridizes to the anti-sense strand at the 3' end of the target sequence. Examples of the preferred primers include sense 5'-GGTACAGGCGGAAACAGACCTT (SEQ ID NO:3); anti-sense 5'-TCCTATTCTCTGACCTACTG (SEQ ID NO:4). The preferred primers can hybridize to and amplify all or a portion of a 2.3 kb HindIII restriction fragment sequence of *S. hyodysenteriae* B204 serotype 2, as shown in FIG. 1.

Once the primers are designed as described above, the primers can be prepared by automated DNA synthesis in accord with standard methods.

Once the target sequence has been identified, the target sequence can serve as a probe or can be used to design other probes. A probe can hybridize to all or a portion of a target sequence, preferably under all stringency conditions. The preferred probes hybridize to all or a portion of a 2.3 kb HindIII partial digest restriction fragment of *S. hyodysenteriae* B204 as shown in FIG. 1. The probes are useful to detect amplified products of the target sequence and to detect and identify at least one serotype of *S. hyodysenteriae*.

A probe can have about 16 to about 2300 nucleotides, more preferably about 25 to 100 nucleotides. A probe can hybridize to all or a portion of a target sequence. If a probe is designed to detect amplified products of the target sequence, it is preferably designed not to hybridize to the sequence of primers used for amplification. A probe designed to detect amplification products can preferably hybridize to sequences between the primer sequences. A probe can hybridize to the DNA strand with coding sequence and is designated a sense probe. A probe can hybridize to the DNA strand that is complementary to the strand with the coding sequence and is designated an anti-sense probe. A probe can be designed to hybridize to mRNA complementary to the target sequence.

Hybridization conditions for forming hybrids for a probe of about 16 to 100 nucleotides or more without any mismatches are preferably those described in Flores et al., *J. of Vir.*, 64:4021 (1990). Briefly, immobilized target sequences are incubated at 53° C. for 16 to 32 hours in 4×SSC (1×SSC=0.15M NaCl plus 0.015M sodium citrate), 0.02% sodium dodecyl sulfate, 50% formamide, 50 mM potassium phosphate buffer, 10% Dextran sulfate, 0.02% Ficoll (Pharmacia, Inc., Piscataway, N.J.), 0.02% bovine serum albumin, 0.02% polyvinylpyrrolidone, 20 μg sheared salmon DNA per ml, and the probe. Prehybridizations are carried out in the same buffer minus dextran sulfate. After incubation, the hybrids are washed four times for 5 minutes at room temperature with 0.1% sodium dodecyl sulfate in 2.5×SSC, and then twice for 15 minutes at 53° C. with 0.05% sodium dodecyl sulfate in 1.25×SSC. These conditions can be modified, if necessary, depending on the method of detection employed, such as dot blot hybridization, Southern blot hybridization, or multiwell solution hybridization. Modification of hybridization conditions depending on the method employed are known.

A probe of the invention can be perfectly complementary to the target sequence or can have some mismatches with the target sequence. A probe of about 16 to 20 nucleotides preferably has about 1 to 3 mismatches localized near the 5' or 3' ends of the probe (i.e., within 5 base pairs of either end). Probes of about 20 to 2300 nucleotides can have up to about 30% mismatches and still hybridize to the target sequence. Mismatched probes can still hybridize to the target sequence if conditions of hybridization are modified to account for the mismatch, as, for example, by decreasing melting temperature by about 1.0 to 1.5° C. for every 1% of mismatch. Because a target DNA sequence has been cloned and identified, the effect of mismatches in the probe on $T_M$ (melting temperature) can be determined using a standard method such as described by Maniatis at pages 11.47 to 11.57, which is hereby incorporated by reference.

Probes can also be detectably labeled using a variety of standard methods. The probes can be detectably labeled by incorporating one or more labeled nucleotides into the probe. Nucleotides can be labeled with biotin, with a radiolabel, or with a fluorescent moiety or luminescent moiety and the like.

A preferred probe of the invention can hybridize to all or a portion of a 2.3 kb HindIII restriction fragment of *S. hyodysenteriae* B204 (SEQ ID NO:1) or to amplification products of a 2.3 kb HindIII restriction fragment from serotype B204 and other serotypes. A preferred probe has a sequence as follows:

sense-5'-TAGGGGCTGCTGTTCTAGCTGTAAATGC (SEQ ID NO: 5)

and corresponding with nucleotides 1143-1170 of SEQ ID NO:1 can hybridize to about a 1.5 kb amplification product of *S. hyodysenteriae* B204 and other serotypes and to the 2.3 kb HindIII fragment under low stringency conditions.

Once designed, a probe can be prepared by automated DNA synthesis or by polymerase chain reaction using appropriate primers. The probe can also be prepared by digesting the 2.3 kb insert in pRED3C6 with any one or more of the restriction enzymes shown in Table I.

A probe according to the invention can be used in a method for identifying at least one serotype of *S. hyodysenteriae* or distinguishing *S. hyodysenteriae* from at least one other microorganism. The probes are used in methods such as restriction enzyme, PCR amplification, slot blot, dot blot, and Southern blot analysis of DNA taken from biological samples suspected of containing at least one serotype of *S. hyodysenteriae*. The steps of the method include isolating DNA from a biological sample suspected of containing at least one serotype of *S. hyodysenteriae*, digesting the extracted DNA with at least one restriction enzyme, and detecting any sequence specific to *S. hyodysenteriae* by hybridization to a probe specific for at least one serotype of *S. hyodysenteriae* chromosomal DNA.

The extraction of DNA from a biological sample can be accomplished by standard methods. Elder et al., cited supra. Biological samples can include pure cultures of bacteria isolated by standard microbiological methods or a biological sample suspected of having at least one serotype of *S. hyodysenteriae* as well as other microorganisms. Examples of biological samples include feces, intestinal contents, intestinal mucosal scrapings, fecal swabs and the like. Environmental samples are also biological samples such as manure, manure-contaminated soil, fomites, pits, lagoon water, or effluent from a premises suspected of containing *S. hyodysenteriae*.

The extract is then digested with at least one restriction enzyme. The choice of restriction enzyme is based upon the sequence of the DNA target sequence specific for *S. hyodysenteriae* and the recognition sequence of the restriction enzyme. Recognition sequences for restriction enzymes are known to those of skill in the art. If all or a portion of the DNA sequence of the target sequence for *S. hyodysenteriae* is known, then restriction enzymes can be selected based on that sequence. For example, the sequence of a 2.3 kb HindIII target sequence, shown in FIG. 1, indicates that there is one site where HindIII can cut the sequence. Other restriction enzymes can be selected that can cut the sequence at one or more locations, preferably at about 1 to 3 locations, as shown in Table I.

TABLE I

| | | | | | |
|---|---|---|---|---|---|
| AccI | AciI | AluI | AlwI | AlwNI | ApoI |
| AvaII | BbvI | BccI | BcgI | BfaI | BseRI |
| BslI | BsmI | BsmAI | BsmBI | BsoFI | BspMI |
| BsrI | BsrBI | BsrFI | BsrGI | Cac8I | CjeI |
| CjePI | CviJI | CViRI | DdeI | DpnI | DraI |
| EaeI | EarI | EciI | Eco57I | EcoNI | EcoRI |
| EcoRII | GdiII | HaeIII | HindIII | HinfI | HphI |
| MaeIII | MboII | MmeI | MnlI | MseI | MslI |
| MspI | MspAII | MwoI | NlaIII | NsiI | NspI |
| PstI | PvuII | RsaI | Sau96I | Sau3AI | SexAI |
| SfaNI | SfcI | SspI | TaqI | TaqII | TfiI |
| TseI | Tsp5O91 | Tth111II | | VspI | |

The digested DNA is then contacted with a probe that can hybridize to a target sequence specific for at least one serotype of *S. hyodysenteriae* under conditions of hybridization for a probe of that size and/or sequence complementarity as described previously. The hybridization conditions can be modified as necessary depending on the method of detection of hybrid formation employed including slot blot, dot blot, and/or Southern blot hybridization. The probes are preferably labeled for ease of detection of hybrid formation.

In a preferred version, DNA is extracted from a biological sample such as from an animal suspected of being infected with *S. hyodysenteriae* or from an environmental sample suspected of containing *S. hyodysenteriae* and the extracted DNA is digested with HindIII. The digested DNA extract is optionally separated and contacted with a probe that can hybridize to a target sequence specific for *S. hyodysenteriae* such as a 2.3 kb HindIII restriction fragment of FIG. 1. The preferred probe has a sequence as follows:

sense-5'-TAGGGGCTGCTGTTCTAGCTGTAAATGC (SEQ ID NO: 5)

and is detectably labeled. The presence of *S. hyodysenteriae* is detected by the detection of hybridization of the probe to digested fragments from the biological sample. Methods of detection of hybrids can be utilized depending on the labeled moiety that is attached to the probe, and are standard methods. This method can also be used to distinguish *S. hyodysenteriae* from at least one other microorganism.

2. Recombinant Expression Vectors and Transformed Cells

A target nucleotide sequence that allows for identification of at least one serotype of *S. hyodysenteriae* can be cloned into an expression vector and introduced into suitable host cells to form transformed cells. The transformed cells carrying an expression vector are useful for amplification of all or a portion of a target sequence to provide a probe, to provide any gene products encoded by the target sequence, and/or as vaccine formulations.

A target sequence, such as all or a portion of a 2.3 kb HindIII partial digest fragment from *S. hyodysenteriae* B204

(SEQ ID NO:1), can be cloned into a suitable expression vector such as pUC18, pKC30, pBR322, pKK177-3, pET-3, and the like by standard methods. Commercially available expression vectors provide for cloning for a target sequence into a site of the vector such that the target sequence is operably linked to transcriptional and translational control regions. It is preferred, but not required, that a target sequence is operably linked to an inducible promoter such as the λPL promoter, the lac promoter, the tac promoter, or the $T_7$ promoter, and the like.

The expression vectors can then be introduced into suitable host cells using methods such as calcium phosphate precipitation, liposome mediated transformation, protoplast transformation, electroporation, and the like. Suitable host cells include *E. coli* strains such as *E. coli* DH5α, and avirulent isogenic Salmonella spp. such as *S. typhimurium* deletion mutants lacking adenylate cyclase and cAMP receptor protein, Salmonella mutants in aro genes, and other Salmonella vaccine strains as described in *Bio/Tech,* 6:693 (1988), and the like.

Transformed cells can be screened by a variety of methods including colony hybridization or reactivity with antibodies specific for *S. hyodysenteriae* B204. A transformed cell is an *E. coli* DH5α cell carrying a pUC18 plasmid with a 2.3 kb HindIII restriction fragment insert from *S. hyodysenteriae* B204. A pUC18 plasmid carrying a 2.3 kb HindIII insert from *S. hyodysenteriae* B204 designated pRED3C6, deposited with the American Type Culture Collection in Rockville, Md. has Accession No. 75826.

3. Method for Detection of *S. hyodysenteriae* in a Biological Sample

According to the invention, a biological sample may be analyzed for the presence of *S. hyodysenteriae* by detecting the presence of DNA amplification products from primers that hybridize to a 2.3 kb HindIII partial digest restriction fragment of *S. hyodysenteriae* B204 serotype 2. Compared to other detection methods presently known and used, the invention advantageously provides a method that is highly sensitive in detecting at least one serotype of *S. hyodysenteriae* in a biological sample when it is present in very low concentration, for example, about 1 to 10 organisms per 0.1 gm sample. It is preferred that an about 1.55 kb DNA sequence that lies between two regions of the about 2.3 kb HindIII sequence is amplified. That sequence is unique to all serotypes of *S. hyodysenteriae*, and provides for the specific detection of the spirochete from other closely-related microorganisms including other members of the order Spirochaetales. Thus, this method is also useful to distinguish *S. hyodysenteriae* from at least one other microorganism.

In brief, the DNA amplification products can be detected by (a) extracting DNA from a biological sample; (b) amplifying a target sequence of the extracted DNA to provide DNA amplification products carrying a selected target DNA sequence; and (c) detecting the presence of *S. hyodysenteriae* by detecting the presence of the DNA amplification products.

The biological sample may be, for example, feces, mucosal secretion, mucosal scrapings, mucosal cells, rectal swabs, intestinal wall, intestinal contents, local lymph nodes, and the like. The biological sample may be derived, for example, from an animal infected with *S. hyodysenteriae*, an animal suspected of being a carrier of *S. hyodysenteriae*, an animal being treated for an infection caused by *S. hyodysenteriae*. The biological sample can also be an environmental sample such as manure, manure-contaminated soil, fomites, pits, lagoon water, or effluent from a premises suspected of containing *S. hyodysenteriae*. Animals susceptible to infection with *S. hyodysenteriae* include swine, ratites (such as rheas), rodents such as rats and mice, dogs, birds, poultry, and other wildlife.

The detection method can also be optionally combined with methods for isolation of microorganisms to provide for confirmation of infection with *S. hyodysenteriae* and/or to increase the sensitivity of the assay. For example, *S. hyodysenteriae* present in a biological sample could be separated from other biological material using an antibody attached to a solid support such as a monoclonal antibody attached to immunomagnetic particle, as described by Islam et al., *J. Clin. Micro.,* 30:2801 (1992). The isolated *S. hyodysenteriae* can then be detected using the polymerase chain reaction as described herein.

In a preferred method, the amplification of the DNA sequence is by polymerase chain reaction (PCR), as described in U.S. Pat. No. 4,683,202 to Mullis; Mullis et al., *Cold Spring Harbor Symp. Quanti. Biol.* 51:263 (1986); Mullis and Faloona, *Methods Enzymol.* 155:335 (1987); Saiki et al., *Science* 239:487 (1988b); and Chien et al., *J. Bacteriol.* 127:1550 (1976). In brief, the DNA sequence is amplified by reaction with at least one oligonucleotide primer or pair of oligonucleotide primers that hybridize to the target sequence or a flanking sequence of the target sequence and a DNA polymerase to extend the primer(s) to amplify the target sequence. The amplification cycle is repeated to increase the concentration of the target DNA sequence.

The biological sample is first treated to extract a nucleic acid sequence specific to *S. hyodysenteriae*, which may be either mRNA or DNA. The nucleic acid fragments may be extracted from the biological sample by standard methods as described in Elders et al., cited supra. Either purified chromosomal DNA or total DNA or total mRNA is extracted from the biological sample for amplification and detection.

In addition, the polymerase chain reaction may be used to amplify cDNA that has been synthesized in vitro by reverse transcriptase of an mRNA template, according to standard methods. The mRNA that is extracted from the biological sample for synthesis of cDNA sequence is suspected of including a messenger RNA that is complementary to a target sequence such as a 2.3 kb HindIII partial digest restriction fragment of *S. hyodysenteriae* B204. Primers useful to generate cDNA can be designed as described previously.

Other methods of polymerase chain reaction using various combination of primers including a single primer to about 3 primers are known to those of skill in the art and are described in Maniatis, cited supra. Those methods include asymmetric PCR, PCR using mismatched or degenerate primers, reverse transcriptase PCR, arbitrarily primed PCR (Welsh et al., *Nucleic Acids Res.,* 18:7213 (1990)), or RAPD PCR, IMS-PCR (as described by Islam et al., *J. Clin. Micro.,* 30:2801 (1992)), multiwell PCR (ELOSA) (as described by Luneberg et al., *J. Clin. Micro.* 31:1088 (1993) and Katz et al., *Am. J. Vet. Res.,* 54:2021 (1993). The methods also include amplification using a single primer as described by Judd et al., *Appl. Env. Microbiol.,* 59:1702 (1993).

The nucleotide sequences are recovered from the biological sample so as to be substantially free of substances that may interfere with the enzymatic amplification procedure, as for example, enzymes, low molecular weight substances such as peptides, proteins, lipids, carbohydrates, and the like. Such methods are known and used in the art.

In a preferred version, an oligonucleotide primer pair that can hybridize to the 2.3 kb HindIII restriction fragment of *S. hyodysenteriae* B204 shown in FIG. 1 are mixed with deoxynucleotides, Taq polymerase, and the extracted DNA or cDNA. Initial denaturing is at 95° C. for 60 seconds followed by 30 cycles with 60 seconds at 65° C. and 120 seconds at 72° C. Amplified products are optionally separated by methods such as agarose gel electrophoresis. The amplified products can be detected by either staining with ethidium bromide silver stain or by hybridization to a probe as described previously. The preferred oligonucleotide primer pairs amplify a portion of the target sequence of *S. hyodysenteriae* B204 of FIG. 1 to form an about 1.5 kb amplification product.

In an alternative embodiment, at least one probe that hybridizes to the amplified products is labeled with a biotin moiety and/or at least one probe labeled with fluorescently labeled probe. The hybrids are then bound to a solid support such as a bead, multiwell plate, dipstick or the like that is coated with streptavidin. The presence of bound hybrids can be detected using an antibody to the fluorescent tag conjugated to horseradish peroxidase. The enzymatic activity of horseraddetectedxidase can be detected with a colored, luminescent or fluorimetric substrate. Conversion of the substrate to product can be used to detect and/or measure the presence of *S. hyodysenteriae* PCR products.

An oligonucleotide primer preferably has a gene sequence that hybridizes to a sequence flanking one end of the DNA sequence to be amplified. The DNA sequence to be amplified is located adjacent the attachment of the single primer, or between the attachment of the two primers. In the use of a pair of oligonucleotide primers, each of the primers has a different DNA sequence and hybridizes to sequences that flank either end of the target sequence to be amplified. Design of primers and their characteristics have been described previously. The preferred DNA sequence of the oligonucleotide primer is positive-sense 5'-GGTACAGGCGGAAACAGACCTT (SEQ ID NO:3), or negative-sense 5'-TCCTATTCTCTGACCTACTG (SEQ ID NO:4), or a complement thereof, or a mixture thereof. The primer may also be a degenerate primer that hybridizes to the target gene sequence under hybridization conditions for a primer of that size and sequence complementarity.

For the binding and amplification, the sample DNA is provided in an aqueous buffer formulated with an effective amount of a divalent cation which is preferably $MgCl_2$, preferably at a concentration of about 0.05–5 mM; an effective amount of DNA polymerase with Taq DNA polymerase being preferred in the form of native purified enzyme or a synthesized form such as Ampli-Taq (available commercially from Perkin-Elmer Cetus Corp., San Francisco, Calif.) an effective amount of dNTPs as a nucleotide source, including, dATP, dCTP, dGTP and dTTP, preferably in a saturating concentration, preferably about 200 uM per dNTP; and an effective amount of one or a pair of oligonucleotide primers. The reaction mixture containing the annealed primer(s) is reacted with a DNA polymerase at about 72° C. for about 1–10 minutes, preferably about 3–5 minutes, to extend the primers to make a complementary strand of the target gene sequence. The cycle is then repeated by denaturing the DNA strands with heat, annealing and extending, preferably for about 25–40 cycles, preferably about 30 cycles.

The major resulting product is preferably an about 1.55 kb gene sequence which termini are defined by the oligonucleotide primer(s), and whose length is defined by the distance between the two primers or the length of time of the amplification reaction. The gene sequence then serves as a template for the next amplification cycle.

The amplified DNA products are optionally separated from the reaction mixture and then analyzed. The amplified gene sequences may be visualized, for example, by separating the gene sequences from undesirable side-products and unreacted reagents by electrophoresis in an agarose or polyacrylamide gel, by HPLC separation in an ion exchange column or size exclusion column, or by the ELOSA technique, and other like techniques known and used in the art.

The amplified gene sequence may be directly or indirectly labelled by incorporation of an appropriate visualizing label, as for example, a radioactive, colorimetric, fluorometric or luminescent signal, or the like. In addition, the gel may be stained before or after electrophoresis with a visualizing dye such as ethidium bromide or silver stain wherein the resulting bands may be visualized under ultraviolet light.

The amplified DNA products may also be detected by Southern blot assay, dot blot assay, slot blot assay, or other like analysis, in which the amplified products are separated by electrophoresis on a polyacrylamide or agarose gel, transferred to a membrane such as a nitrocellulose or nylon membrane, reacted with an oligonucleotide probe, and detected. The amplified products may also be detected by reverse blotting hybridization (dot blot) in which an oligonucleotide probe specific to the gene sequence is adhered to a nitrocellulose or polyvinylchloride (PVC) support such as a multi-well plate, and then the sample containing labelled amplified product is added, reacted, washed to remove unbound substance, and a labelled amplified product attached to the probe or the gene sequence imaged by standard methods. For slot blot analysis, the DNA products may be applied to a nylon membrane using a microfiltration apparatus, and hybridized with a labelled oligonucleotide probe, as described by standard methods.

The PCR amplification products can be detected in a multiwell plate by hybridization to a probe specific for *S. hyodysenteriae* such as described in ELOSA methods by Katz et al., cited supra. For analysis of nucleic acids extracted from more than one biological sample, amplified products of each extract may be placed separately into a different well of a multi-well plate, such as a PVC plate, and coated with a capture molecule such as streptavidin. The amplified products specific for *S. hyodysenteriae* in each well can be preferably detected by hybridization to a probe labelled with a moiety that provides for color change such as a fluorescent-labelled probe. A multi-well plate format allows the screening of many different biological samples in a single plate and can be conducted because of the extreme sensitivity of the PCR assay for detection of 1 to 10 organisms per 0.1 gram of feces or other biological sample. A multi-well format likewise allows for the screening and quantitation of the target sequence of a single sample in a series of dilutions.

In those assays, the amplified products are hybridized with an oligonucleotide probe that hybridizes to the target gene sequence. It is preferred that the oligonucleotide probe is hybridizable to an about 1.5 kb gene sequence located within the about 2.3 kb HindIII partial digest restriction fragment of the chromosomal DNA of *S. hyodysenteriae* B204. The probe is hybridizable to all or a portion of the gene sequence under conditions suitable for a probe of that size and sequence complementarity. The probe can distinguish from other microorganisms and cells in a biological sample. Preferably, the oligonucleotide probe, specific to *S. hyodysenteriae* has the sequence: positive-sense 5'-TAGGGGCTGCTGTTCTAGCTGTAAATGC (SEQ ID NO:5). Other probes including detectably labelled probes may be prepared as described previously.

Excess probe is removed from the reaction vessel or support, for example, by washing with a suitable solution.

The presence or absence of the DNA gene product is then determined by visualization of the label on the membrane or the vessel with an imaging system corresponding to the label that is used, including, for example, autoradiography, radiation counting, X-ray, colorimetric, fluorometric or luminescent signal, and the like.

The detection of amplified gene product in the sample indicates the presence of *S. hyodysenteriae* in the biological sample and in the animal. The method is useful in diagnosing an *S. hyodysenteriae* infection in animals, and for detecting animals that are carrier-shedders of *S. hyodysenteriae* in that they have no outward signs of disease but carry the spirochete internally and shed the organism in feces and other body materials and for detecting *S. hyodysenteriae* in environmental samples contaminated with body fluids from infected animals.

The amplification method is also useful for monitoring the efficacy of treatment for an infection caused by *S. hyodysenteriae* to ensure that subclinically infected or carrier-shedder animals are not formed. For example, the assay may monitor the effectiveness of treatment of an animal with an antimicrobial agent such as carbadox, tiamulin, lincomycin, arsanilic acid, chlortetracycline, oxytetracycline, bacitracin, pyrantel tartrate, fenbendazole, gentamicin, neomycin, roxarsone, tylosin, sulfamethazine, virginiamycin, and the like, or a disinfection of the environment using agents such as chlorhexidine, formaldehyde, cresols, phenols and quaternary ammonium compounds among other treatments. In that method, biological samples such as feces, rectal swabs, mucosal scrapings, environmental samples, and the like, are obtained from an animal under treatment for an infection caused by *S. hyodysenteriae* or the environment of the animal, and DNA amplification products of a target sequence of *S. hyodysenteriae* from those samples are analyzed for the presence of the *S. hyodysenteriae*. Samples are obtained from the animal from time to time on a routine basis over the course of treatment, or afterwards, preferably about every day following treatment. The method can be used to monitor the efficacy of disinfection of equipment, fomites and the environment surrounding an animal infected with *S. hyodysenteriae*.

4. Vaccine.

A 56 kDa polypeptide and nucleotide sequence of a 2.3 kb fragment of *S. hyodysenteriae* B204 shown in FIG. 1 are useful in formulating vaccines for immunizing animals against infection by *S. hyodysenteriae*. The polypeptide is also useful in stimulating antibodies specifically reactive with all the serotypes of *S. hyodysenteriae* and not with other closely related non-pathogenic intestinal spirochetes. The vaccine contains an amount of the 56 kDa polypeptide effective to elicit a protective immune response against *S. hyodysenteriae* in the animal, and achieving clinical efficacy, by stimulating the production of antibodies specifically reactive with *S. hyodysenteriae*, exemplified by monoclonal antibody 10G6/G10 (available from Dr. Duhamel at University of Nebraska, Lincoln, Nebr.). The effectiveness of the vaccine is due, at least in part, to the conservative nature of the nucleotide sequence encoding the 56 kDa polypeptide between different serotypes of *S. hyodysenteriae* and to its uniqueness to *S. hyodysenteriae*.

The vaccine is composed of a substantially pure, 56 kDa polypeptide encoded on an about 2.3 kb HindIII restriction fragment of the chromosomal DNA of *S. hyodysenteriae*, exemplified by the chromosomal DNA of *S. hyodysenteriae* isolate B204 shown in FIG. 1. The 56 kDa protein has a predicted amino acid sequence shown in FIG. 1 (SEQ ID NO:2). As used herein, the term "substantially pure" means that the polypeptide has been extracted and isolated from its natural association with other proteins, lipids, and other like substances from an appropriate host system. Preferably, the DNA fragment has the nucleotide sequence shown in FIG. 1 (SEQ ID NO:1).

The polypeptide may be produced, for example by incorporating the DNA restriction fragment into an expression vector, which includes the restriction fragment operably linked to transcriptional and translational control regions in the vector. The expression vector may then be used to form a transformed cell that includes the DNA fragment which can be used to produce the 56 kDa polypeptide, as described previously. The 56 kDa polypeptide has a predicted amino acid sequence as shown in FIG. 1 (SEQ ID NO:2). A plasmid designated pRED3C6 and carrying the 2.3 kb HindIII insert from *S. hyodysenteriae* B204 has been deposited with the American Type Culture Collection, Rockville, Md., and given Accession No. 75826.

The polypeptide is administered in combination with a physiologically-acceptable, non-toxic, liquid carrier, compatible with the polypeptide and the animal. Suitable pharmacological carriers include, for example, physiological saline (0.85%), phosphate-buffered saline (PBS), Tris (hydroxymethyl aminomethane (TRIS), Tris-buffered saline, and the like.

The vaccine may further include an adjuvant to enhance the immune response in the animal. Such adjuvants include, for example, aluminum hydroxide, aluminum phosphate, Freund's Incomplete Adjuvant (FCA), liposomes, ISCOMs (Mowat et al., *Immunology Today*, 12:383 (1991)), EMULSIGEN PLUS, and the like. The vaccine may also include additives such as buffers and preservatives to maintain isotonicity, physiological pH, stability, and sterility. Parenteral and intravenous formulations of the vaccine may include an emulsifying and/or suspending agent, together with pharmaceutically-acceptable diluents to control the delivery and the dose amount of the vaccine. Other additives may be included as desired, as for example, preservatives, buffering agents, and the like.

The vaccine may be used for alleviating or minimizing the symptoms of an infection caused by *S. hyodysenteriae*. The vaccine may be delivered to the animal, for example, by parenteral delivery, injection (subcutaneous or intramuscular), oral, intrarectal, and the like, by known techniques in the art. For prophylactic and anti-infectious therapeutic use in vivo, the vaccine contains an amount of the polypeptide to stimulate a level of active immunity in the animal to inhibit and/or eliminate *S. hyodysenteriae* pathogenesis.

Factors bearing on the vaccine dosage include, for example, the age and weight of the animal. The range of a given dose is about 1 to 1000 μg of the purified polypeptide per ml, preferably about 50–200 μg/ml preferably given in about 1–5 ml doses. The vaccine should be administered to the animal in an amount effective to ensure that the animal will develop an immunity to protect against infection by *S. hyodysenteriae*. For example, for an about 20–30 lb swine, a single dose of a vaccine made with Freund's incomplete adjuvant for subcutaneous or intramuscular injection, would contain about 50–200 μg of the purified polypeptide per ml. Preferably, the vaccine is given in an about 1–5 ml dose before or at the time of weaning (2–4 weeks old). The immunizing dose would then be followed by a booster injection given at about 14–28 days after the first injection.

The invention also provides for a vaccine formulation of a live avirulent microorganism transformed with a vector having a 2.3 kb DNA fragment insert from *S. hyodysenteriae*

B204 having a nucleotide sequence as shown in FIG. 1. The fragment can be inserted in to a suitable expression vector such as pYA292, as described previously. Plasmid pYA292 carries a Salmonella origin of replication, an asd gene as the only selectable marker gene, $P_{trc}$ regulator/promoter, a ribosome binding site, and an ATG start codon followed by a multiple cloning site and transcriptional terminators. Plasmid pYA292 is designed to express a recombinant antigen as a non-fusion protein.

An expression vector carrying an insert can be transformed into an avirulent immunogenic host cell such as Salmonella spp. having attenuating mutations in genes encoding enzymes involved in the synthesis of vital metabolites such aro, cya, crp, and asd as described by Curtis et al., *Infection and Immunity*, 55:3035 (1987); Dugan et al., *J. Infec. Dis.*, 158:1329 (1988); and Edwards et al., *J. Bacteriol.*, 170:3991 (1988). These microorganisms have the capacity to elicit long-lasting humoral and cell mediated immunity at high levels of safety.

The Salmonella spp. transformed with a vector carrying a 2.3 kb insert from *S. hyodysenteriae* can be screened for reactivity with antibodies to *S. hyodysenteriae* or by hybridization of DNA or mRNA to a probe specific for the 2.3 kb insert. Transformed Salmonella spp. producing a polypeptide encoded by the 2.3 kb insert (SEQ ID NO:1) can be further selected for avirulence and for generating a protective immune response against *S. hyodysenteriae* in an animal. Animals include swine, poultry, ratites, rodents, birds, rheas, and the like. The transformed microorganism that is avirulent and elicits a protective response against *S. hyodysenteriae* infection in an animal is the preferred microorganism for the vaccine formulation.

The microorganisms can be combined with carriers or adjuvants as described previously. The vaccine can be administered parenterally, e.g. subcutaneously, intraperitoneally or intramuscularly, orally or intrarectally. Preferably, the vaccine is administered orally at least one and preferably at least two or more times at intervals of about 14 to 28 days.

The amount of microorganism included in the vaccine formulation is an amount that is effective to generate a protective immune response against infection with *S. hyodysenteriae* as determined by detecting a decrease in the mortality and/or symptoms of disease caused by *S. hyodysenteriae*. The amount of microorganisms will depend, in part, on the route of administration and/or the animal to immunized. Preferably, an amount of microorganisms is about $10^5$ to $10^{10}$ CFU/ml and more preferably about $10^6$ to $10^9$ CFU/ml.

Passive Immunization.

The polypeptide may also be utilized to raise polyclonal antibody sera and monoclonal antibodies for use in passive immunization therapies. Polyclonal antibodies may be raised to the polypeptide by hyperimmunizing an animal with an inoculum containing the isolated 56 kDa polypeptide. The blood serum may be removed and contacted with immobilized 56 kDa polypeptide reactive with the protein-specific antibodies. The semi-purified serum may be further treated by chromatographic methods to purify IgG and IgM immunoglobulins to provide a purified polyclonal antibody sera for commercial use.

Monoclonal antibodies reactive with the polypeptide may be raised by hybridoma techniques known and used in the art. In brief, a mouse, rat, rabbit or other appropriate species may be immunized with the 56 kDa polypeptide. The spleen of the animal is then removed and processed as a whole cell preparation. Following the method of Kohler and Milstein (*Nature* 256:496–97 (1975)), the immune cells from the spleen cell preparation can be fused with myeloma cells to produce hybridomas. The hybridomas may then be cultured and the culture fluid tested for antibodies specific for the 56 kDa polypeptide using, for example, an ELISA in which the 56 kDa polypeptide is immobilized onto a solid surface and act as capture antigens. The hybridoma may then be introduced into the peritoneum of the host species to produce a peritoneal growth of the hybridoma, and ascites fluids containing the monoclonal antibody specific to the spirochete may be collected.

The monoclonal antibodies may be used in diagnostic and therapeutic compositions and methods, including passive immunization. Immunoglobulins specific towards the 56 kDa polypeptide may be used to provide passive immunity against an infection caused by *S. hyodysenteriae*. Animals may be treated by administering immunoglobulins intramuscularly at about 100/mg/kg body weight, about every 3–7 days.

Diagnostic Method.

Antibodies to the 56 kDa polypeptide may be used in an in vitro method of diagnosing an infection of *S. hyodysenteriae* in an animal. The diagnostic method includes contacting a body material potentially containing *S. hyodysenteriae* such as feces, mucosal scraping, or other like tissue sample or body material with a labelled antibody raised to the 56 kDa polypeptide encoded on an about 2.3 kb HindIII restriction fragment of *S. hyodysenteriae*, and detecting the label in the complex formed between the polypeptide in the body material and the labelled antibody. The method may also be performed by combining the body sample with the antibody to the polypeptide, and then contacting the sample with a labelled anti-species antibody reactive with the polypeptide-specific antibody, and then detecting the label.

In addition, the 56 kDa polypeptide may be used as a capture antigen in a method of monitoring and profiling an infection caused by *S. hyodysenteriae*. For example, the polypeptide may be used in an ELISA technique by immobilizing the polypeptide on a solid support such as a polyvinylchloride plate, and contacting the immobilized peptide with a sample material to react with and detect antibodies present in the sample.

The invention further provides an in vitro assay for detecting *S. hyodysenteriae*-specific antibodies in a sample. In that method, a sample to be tested is contacted with a composition containing the about 56 kDa polypeptide, which is preferably labelled, to form a conjugate which is then detected. A method for diagnosing an infection by *S. hyodysenteriae* in a biological sample may be carried out with the polyclonal antibody sera or monoclonal antibodies described hereinabove, in an enzyme-linked immunosorbant assay (ELISA), radioimmunoassay (RIA), immunofluorescent assay (IFA), a Northern, Western or Southern blot assay, and the like. In brief, the antibody or biological sample (i.e., tissue sample, body fluid) may be immobilized, for example, by contact with a polymeric material such as polystyrene, polyvinylchloride, a nitrocellulose paper, or other like support means for immobilizing the antibody or sample. The other antibody or biological sample is then added, incubated, and the non-immobilized material is removed by washing or other means. A labeled species-specific antibody reactive with the latter is added. The serum antibody or *S. hyodysenteriae* bacteria in the biological sample, is then added and the presence and quantity of label is determined to indicate the presence and amount of *S. hyodysenteriae* bacteria in the biological sample.

5. Mutants of *S. hyodysenteriae* and Vaccine Composition

Once a target sequence specific for *S. hyodysenteriae* and that can distinguish at least one serotype of *S. hyodysente-*

*riae* from other closely related microorganisms is identified, the target sequence can be altered or mutated to form mutants of *S. hyodysenteriae*. An example of a target sequence found in all serotypes of *S. hyodysenteriae* and not in other closely-related microorganisms is a 2.3 kb HindIII restriction fragment of *S. hyodysenteriae* serotype B204 having the nucleotide sequence shown in FIG. 1. *S. hyodysenteriae* B204 mutants with alterations in the sequence shown in FIG. 1 can be generated using standard methods. Mutants with alterations or deletions in this region can be selected for reduced virulence and/or the ability to stimulate an immune response, preferably a protective immune response to infection with *S. hyodysenteriae* serotypes. These mutants can be useful in vaccine formulations and to elicit antibodies in animals without causing mortality. The antibodies elicited could be used for passive immunization.

Mutants of *S. hyodysenteriae* B204 with alterations in the 2.3 kb HindIII restriction fragment can be generated using standard methods such as chemical mutagenesis (as described in U.S. Pat. No. 4,999,191 to Glisson et al.); transposon mediated mutagenesis (as described in U.S. Pat. No. 4,764,370 to Fields et al.); ultraviolet irradiation; and methods of site-specific mutagenesis (as described in Maniatis et al., cited supra).

Mutant microorganisms can be screened for alteration to the target sequence in a 2.3 kb HindIII restriction fragment using a variety of methods. The mutant can be screened preferably for lack of production of a functional gene product encoded by a 2.3 kb HindIII restriction fragment by lack of reactivity with an antibody specific for all or a portion of the polypeptide encoded by the fragment as exemplified by monoclonal antibody 10G6/G10 or polyclonal antibodies to the peptides, as described in Example VI. The mutants can also be screened for an inability to hybridize to a 2.3 kb HindIII restriction fragment probe or a change in the restriction enzyme fragments that hybridize to the probe. Other screening methods, such as using PCR and sequencing of the mutated fragment, can also be employed.

Alterations or mutations to the target sequence include nucleotide substitutions, deletions, additions (i.e., especially insertion of a transposon) in the 2.3 kb HindIII restriction fragment of serotype B204. Once mutants with alterations to the sequence are identified, they can be further selected for reduced virulence in animals and for the ability to elicit an immune response, preferably a protective immune response, using standard methods. The especially preferred mutants have a deletion of a portion of a 2.3 kb HindIII restriction fragment, have reduced virulence for animals, and elicit a protective immune response that inhibits wild-type *S. hyodysenteriae* infection with at least one serotype of *S. hyodysenteriae*.

The mutants of the invention are useful to elicit antibodies in animals without causing mortality. These antibodies can be useful in methods of passive immunization as described previously.

The mutants of the invention can also be useful in vaccine formulation. A vaccine formulation includes an amount of a mutant of *S. hyodysenteriae* having reduced virulence for animals effective to inhibit *S. hyodysenteriae* infection in animals, wherein the mutation is an alteration of a 2.3 kb HindIII restriction fragment of *S. hyodysenteriae* B204 in admixture with a physiologically acceptable carrier. The mutant microorganism is administered in combination with a physiologically acceptable, non-toxic liquid carrier compatible with the microorganism and the animal. Suitable pharmacological carriers include, for example, physiological saline (0.85%), phosphate buffered saline, Tris (hydroxymethylamino methane), Tris buffered saline, and the like.

The vaccine may further include an adjuvant to enhance the immune response in the animal. Such adjuvants include, for example, aluminum hydroxide, aluminum phosphate, Freund's incomplete adjuvant, liposome, ISCOMs, EMULSIGEN, and the like. The vaccine may also include additives such as buffers and preservatives to maintain isotenicity physiological pH instability. Parenteral and intravenous formulations of the vaccine may include emulsifying and/or suspending agent together with pharmaceutically acceptable diluents to control the delivery and dose amount of the vaccine.

The vaccine may be used for alleviating or minimizing the symptoms of disease caused by *S. hyodysenteriae*. The vaccine may be delivered to the animal, for example, by parenteral delivery, injection (subcutaneous or intramuscular), or oral delivery by techniques known in the art. For prophylactic and anti-infectious therapeutic use in vivo, the vaccine contains an amount of the microorganism effective to stimulate a level of active immunity in the animal to inhibit and/or eliminate *S. hyodysenteriae* pathogenesis.

Factors bearing on the vaccine dosage include, for example, the age and weight of the animal. The range of a given dose is about $10^5$ to $10^{10}$ CFU of the microorganism per ml, preferably about $10^6$ to $10^9$ CFU/ml, preferably given in about 1 to 5 ml doses. The vaccine can be administered to the animal as a single dose but is preferably administered as 2 or 3 doses over an 8–10 week period.

The invention will be further described by reference to the following detailed examples, wherein the methodologies are as described below. These examples are not meant to limit the scope of the invention that has been set forth in the foregoing description. Variation within the concepts of the invention are apparent to those skilled in the art. The disclosures of the cited references throughout the specification are incorporated by reference herein.

EXAMPLE I

Bacterial Culture and Growth Conditions

Several genera of bacteria were cultured and grown to provide nucleic acid samples for analysis by polymerase chain reaction and Southern blot hybridization with the 2.3 kb HindIII DNA fragment of clone pRED3C6.

1. Bacterial Strains.

*Serpulina hyodysenteriae* strain B78 serotype 1 (ATCC# 27164; Harris et al., *Int. J. Syst. Bact.*, 29:102–109 (1979); and Kinyon et al., Infect. Immun., 15:638–646 (1977)), strain B204 serotype 2, strain B169 serotype 3, and strain A1 serotype 4, were obtained from J. M. Kinyon, College of Veterinary Medicine, Iowa State University, Ames, Iowa. Reference *S. hyodysenteriae* strains B234 serotype 1, B8044 serotype 5, B6933 serotype 6, AcK 300/8 serotype 7 were provided by L. A. Joens, Department of Veterinary Science, University of Arizona, Tucson, Ariz. Reference strains FM-88-90 serotype 8, FMV 89-3323 serotype 9 were provided by M. Jacques, Faculté de Médecine Vétérinaire, Université de Montréal, Saint-Hyacinthe, Québec, Canada. Li et al., *J. Clin. Microbiol.*, 29:2794–2797 (1991). The reference isolates for WBHIS, *Serpulina innocens*, isolates B256 (ATCC# 29796; and Harris et al., cited supra) and 4/71 were obtained from the American Type Tissue Culture Collection, Rockville, Md., and T. B. Stanton, National Pig Disease Center, Ames, Iowa, respectively.

A total of 13 field isolates representing three genotypic groups of WBHIS distinct from *S. innocens* were obtained from porcine feces, porcine rectal swabs, and porcine colonic mucosal scrapings submitted either to the Veterinary Diagnostic Center, University of Nebraska-Lincoln or Agriculture Canada, Saint-Hyacinthe, Quebec. Lee et al., *Vet. Microbiol.*, 34:35–46 (1993); and Ramanathan et al., *Vet. Microbiol.*, 37:53–64 (1993). The WBHIS isolates B359 and B1555a were obtained from J. M. Kinyon, and isolate D9201243A was provided by R. L. Walker, California Veterinary Diagnostic Laboratory System, University of California, Davis, Calif. The WBHIS isolate 16 (ATCC# 49776; Jones et al., *J. Clin. Microbiol.*, 24:1071–1074 (1986)) obtained from an HIV-positive homosexual male with diarrhea was provided by R. M. Smibert, Virginia Polytechnic Institute, Blacksburg, Va. In addition, species of other genera of bacteria were obtained and cultured accordingly to standard methods as described below. In some instances, chromosomal DNA was obtained.

*Treponema succinifaciens*, isolate 6091 (ATCC# 33096; Cwyk et al., *Arch. Microbiol.*, 122:231–239 (1979)) and Bacteroides vulgatus (ATCC# 31376) were obtained from the American Type Tissue Culture Collection. Chromosomal DNA from *Spirochaeta aurantia* was provided by E. P. Greenberg, University of Iowa, Iowa City, Iowa. The *Treponema pallidum* chromosomal DNA was provided by M. V. Norgard, The University of Texas Health Science Center, Houston, Tex. Chromosomal DNA from representative stains of each of the ten genetic groups in the family Leptospiraceae including *Leptospira biflexa* serovars patoc, semaranga, and codice, *Leptospira interrogans* serovars icterohaemorrhagiae, fortbragg, ballum, celledoni, lyme, and borincana, and *Leptonema illini* serovar illini were provided by R. L. Zuerner, National Pig Disease Center, Ames, Iowa. Chromosomal DNA from *Borrelia burgdorferi*, *Campylobacter coli* and *C. hyointestinalis* were provided by M. P. Murtaugh, University of Minnesota, St. Paul, Minn. Isolates of *Salmonella choleraesuis* and *S. typhimurium* were provided by P. J. Fedorka-Cray, National Pig Disease Center, Ames, Iowa. The *Escherichia coli* DH5α was purchased from a commercial source (GIBCO-BRL, Gaithersburg, Md.).

2. Medium and growth conditions.

For isolation of DNA, cultures of Serpulina spp., WBHIS, and *T. succinifaciens* were propagated in pre-reduced anaerobically-sterilized (PRAS) trypticase soy broth supplemented with 0.5% (wt/vol) glucose (Sigma Chemical Co., St. Louis, Mo.), 0.05% (wt/vol) cysteine hydrochloride monohydrate (Sigma), 1.0% (wt/vol) yeast extract (BBL Microbiology Systems, Becton Dickinson and Co., Cockeysville, Md.), 2.0% (v/v) bovine fetal serum (HyClone Laboratories, Inc., Logan, Utah), 0.2% (wt/vol) sodium bicarbonate and 5.0% (v/v) sterile porcine fecal extract as described by Kunkle et al., *J. Clin. Microbiol.*, 24:669–671 (1986), except that 1% (vol/vol) of room air was injected at the time of inoculation (Stanton et al., *Vet Microbiol.*, 18:177–190 (1988)). Broth cultures were grown to late logarithmic phase in 5 ml volumes in Hungate tubes or in 250 ml volumes in serum bottles. Cultures were stirred constantly using a magnetic stirrer at 37° C. under a 10% hydrogen, 10% carbon dioxide and 80% nitrogen atmosphere for 48 to 72 hours. Cultures of Salmonella spp., Bacteroides vulgatus and *Escherichia coli* were grown at 37° C. with shaking in Luria-Bertani broth to late logarithmic phase.

Chromosomal DNA was purified as previously described by Ramanathan et al., *Vet. Microbiol.*, 57:53–64 (1993), except that the final pellet was resuspended in sterile $H_2O$ to a final concentration of 12.5 ng/μl.

EXAMPLE II

Library Construction and Recombinant Screening

A library of *S. hyodysenteriae* isolate B204 in *E. coli* DH5α was constructed.

1. Preparation of the DNA Library.

*Serpulina hyodysenteriae* isolate B204 and weakly β-hemolytic intestinal spirochetes of swine; isolates B359 and B1555a (courtesy of J. M. Kinyon, College of Veterinary Medicine, Iowa State University, Ames, Iowa); *Serpulina innocens* isolate B256 (American Type Culture Collection, Rockville, Md.); and *E. coli* strain DH5α (Bethesda Research Laboratories, Inc., Gaithersburg, Md.) were used. Serpulina spp. and other spirochetes were propagated in FS medium (Kunkle et al., *J. Clin. Microbiol.*, 24:669–671 (1986)) to a density of $10^8$ to $10^9$ cells per ml at 37° C.

DNA was isolated, by a modification of a previously reported method (Caputa et al., *J. Clin. Microbiol.*, 29:2418–2413 (1991)), from a 500 ml culture of *S. hyodysenteriae*, isolate B204. Briefly, spirochetes were centrifuged, washed twice in 100 ml of TE buffer (10 mM Tris-HCl [pH 8.0], 1 mM $Na_2$EDTA [pH 8.0]), and resuspended in 25 ml of 50 mM Tris-HCl (pH 8.0), 50 mM $Na_2$EDTA (pH 8.0). N-lauroylsarcosine was added to a final concentration of 2% (wt/vol), followed by the addition of 100 μg/ml of proteinase K. The mixture was incubated at 56° C. for 16 hours. Phenylmethylsulfonyl fluoride was added to a final concentration of 1 mM and the mixture was incubated at room temperature for 10 minutes, then the solution was mixed with 0.1 volume of 7.5M ammonium acetate, and the DNA was precipitated with 2 volumes of ethanol. The DNA precipitate was recovered on a glass rod, washed with 70% ethanol, resuspended in TE buffer to a concentration of 0.5 to 1 μg/μl and stored at −20° C. until needed.

Standard cloning protocols were used for DNA manipulations. Sambrook et al., *Molecular Cloning: A Laboratory Manual*, 2nd ed., Cold Spring Harbor Laboratory, Cold Spring Harbor, N.Y. (1989). Purified chromosomal DNA from *S. hyodysenteriae*, isolate B204 was incompletely digested with HindIII (Stratagene, LaJolla, Calif.) and 4 kb to 9 kb fragments were obtained by centrifugation on a 5% incremental sucrose gradient with a range of 10 to 40%. After dialysis against TE buffer, the DNA fragments were ligated with T4 DNA ligase (Stratagene, LaJolla, Calif.) to plasmid vector pUC18 (Bethesda Research Laboratories, Inc., Gaithersburg, Md.) dephosphorylated with calf intestinal alkaline phosphatase (Bethesda Research Laboratories, Inc., Gaithersburg, Md.). *E. coli*, strain DH5α cells were transformed with the ligation mix and recombinant clones were selected by growth on Luria-Bertani (LB) agar containing 100 μg/ml ampicillin (Bethesda Research Laboratories, Inc., Gaithersburg, Md.), 12 μg/ml isopropyl-β-D-thiogalactosidase (IPTG) (Bethesda Research Laboratories, Inc., Gaithersburg, Md.), and 40 μg/ml 5-bromo-4-chloro-3-indoyl-β-D-galactoside (X-gal) (Bethesda Research Laboratories, Inc., Gaithersburg, Md.). Replica plating was executed by transferring colonies to nitrocellulose membranes (HAFT, 0.45 μm pore size) (Millipore Corp., Bedford, Mass.).

Transformed *E. coli* DH5α cells were screened with monoclonal antibodies, such as 10G6/G10, by colony immunoblotting. These monoclonal antibodies can be prepared as described in Example VI or are available from Dr.

Duhamel, University of Nebraska, Lincoln, Nebr. A monoclonal antibody used for screening has been designated 10G6/G10 and is an IgM antibody that is specific for cell free supernatants derived from *S. hyodysenteriae*. Briefly, replica membranes (Millipore cat. #HATF 137 50, Millipore Corp., Bedford, Mass.) were lysed in chloroform vapor followed by overnight incubation in lysis/blocking solution (5% nonfat dry milk, 0.5M $MgCl_2$, 40 mg/ml lysozyme, 100 mg/ml chloramphenicol, 2 mg/ml DNase) at room temperature. Membranes then were incubated sequentially at room temperature with ascites fluid for 2 hours, followed by biotin-labeled goat anti-mouse [IgA+IgG+IgM(H+L)] antibody (Kirkegaard and Perry Laboratories Inc., Gaithersburg, Md.) for 1 hour, peroxidase-labeled streptavidin (Kirkegaard and Perry) for 45 minutes, and 4-Chloro-l-Naphthol (Kirkegaard and Perry) for 5 minutes. Five 5-minute washes with wash buffer (1M Tris-base, 2M NaCl, 5% nonfat dry milk and 0.05% NP-40 (pH 7.5)) were performed between each incubation step. One immunopositive clone, designated pRED3C6, was identified based on development of a dark purple precipitate.

EXAMPLE III

DNA Sequencing and Primer Selection

The immunopositive clone was amplified and the plasmid DNA with insert was isolated and sequenced. The insert was identified as about a 2.3 kb HindIII partial digest fragment. The nucleotide sequence of the 2.3 kb insert fragment was used to design primers.

1. Plasmid and insert DNA isolation and sequencing.

The recombinant plasmids were isolated (Magic™ Minipreps, Promega Corp., Madison, Wis.), digested with the restriction enzyme HindIII (GIBCO-BRL), and the DNA fragments separated by electrophoresis in a 0.8% agarose gel using TAE running buffer (16 mM Tris-base, 8 mM sodium acetate, and 1 mM EDTA, pH 7.5) containing 0.66 μg of ethidium bromide per ml. The resulting bands were visualized and photographed under ultraviolet light with a Polaroid MP 4 Land camera. Recombinant DNA bands were excised from the gels with a razor blade, isolated (Geneclean II, BioRad, Richmond, Calif.), and subjected to the restriction enzymes AccI, AluI, EcoRI, DraI, HaeIII, SspI and XbaI (GIBCO-BRL). Resulting fragments were purified and subcloned into the vector pUC18 for sequencing using a Model 4,000 DNA sequencer (Li-Cor, Inc. Lincoln, Nebr.). Sequencing data were analyzed and assembled using the Program manual for the GCG Package Version 7, April 1991 from the Genetics Computer Group (1991). Results are shown in FIG. 1.

Presence of −10 and −35 sequences along with a probable ribosomal binding site upstream from the transcription start codon of the gene suggested a single protein transcript. Analysis of the deduced amino acid sequence of the ORF for prediction of a membrane translocation signal failed to identify any significant homology with other known N-terminal export signal sequences. However, the C-terminal sequence of the gene contained a highly charged amino acid followed by a Ser Thr-rich amphophilic region suggestive of an extracellularly secreted protein. Lory, *J. Bacteriol.*, 174:3423–3428 (1992). The sequence encodes a polypeptide with a predicted molecular weight of a 56 kDa protein. The nucleotide sequence may also encode related polypeptides of smaller molecular weight that could be post-translationally processed.

Furthermore, comparisons of the DNA sequence of the recombinant 2.3-kb DNA fragment of pRED3C6 with the sequences of the tly A gene (Muir et al., *Infect. Immun.*, 60:529–535 (1992)), tly B, and tly C gene of *S. hyodysenteriae* (A. Agnes H. M. ter Huurne, *Ph. D. Dissertation*, University of Utrecht, Utrecht, Netherlands, (1993)), and the fla A gene of Koopman et al., *Inf. and Imm.*, 60:2920 (1992) indicated that these sequences had less than 45% nucleotide sequence identity and less that 25% amino acid identity. The nucleotide and amino acid sequences were also compared with nucleotide sequences encoding a 39 kDa protein from *S. hyodysenteriae*, shown in ML Technology Ventures' PCT Application No. WO91/04036 published Apr. 4, 1991, and had less than 47% DNA sequence identity and less than 25% amino acid identity. A comparison to sequences published in EP0350715 also showed less than 45% DNA sequence identity and less than 20% amino acid identity. The nucleotide sequence comparison also revealed in most cases that there were little or no regions of contiguous sequence identity of greater than 10 base pairs. The sequence comparisons were conducted using GCG Package, version 7.3, June 1993 (Genetics Computer Group, Madison Wis.). See Table II.

TABLE II

Sequence analysis comparisons between the 2.3-kb fragment of clone pRED3C6 and sequences currently available.†

| Sequence | Gene | Amino acid % Similarity | Amino acid % Identity | Nucleotide % Identity | GAPs |
|---|---|---|---|---|---|
| Muir et al., 1992 | tly A | 55.7 | 24.4 | 44.5 | 8 |
| Ter Huurne et al., 1993 | tly B | 45.4 | 19.9 | 42.2 | 16 |
| Ter Huurne et al., 1993 | tly C | 42.0 | 19.5 | 44.4 | 20 |
| Koopman et al., 1993 | fla A | 42.6 | 14.8 | 44.1 | 11 |
| ML Tech. Vent., 1991 | Copy #1 | 42.9 | 18.2 | 44.6 | |
| | Copy #2 | 47.1 | 19.9 | 43.2 | |
| | Copy #3 | 44.7 | 19.8 | 44.4 | |
| | Copy #4 | 43.3 | 17.2 | 43.6 | |
| | Copy #5 | 42.9 | 19.0 | 43.1 | |
| | Copy #6 | 42.8 | 18.8 | 41.2 | |
| | Copy #7 | 42.9 | 21.6 | 45.0 | |
| | Copy #8 | 43.7 | 19.8 | 46.5 | |
| ML Tech. Vent., 1990 | 38 kDa | 46.0 | 17.0 | 42.0 | |
| | 60 kDa | 43.6 | 18.4 | 41.7 | |

†Gap, In: Genetics Computer Group. 1991. Program Manual for the GCG Package, Version 7.3, June 1993, 575 Science Drive, Madison, Wisconsin 53711, p. 5–27 to 5–53.

Additionally, an exhaustive search of the EMBL database failed to identify any sequence with significant DNA or amino acid homology with the recombinant 2.3 kb HindIII DNA fragment and its deduced amino acid sequence.

While not meant to limit the invention in any way, there is evidence that the 56 kDa polypeptide encoded by the recombinant 2.3 kb DNA fragment of pRED3C6 represents a putative *S. hyodysenteriae* hemolysin distinct from those described previously. This evidence indicates that transformation of a non-hemolytic *E. coli* host with pRED3C6 conferred hemolytic activity to the *E. coli* host. Cleavage and subcloning of the ORF of the recombinant 2.3 kb DNA fragment resulted in complete loss of hemolytic activity of the *E. coli* host. The fact that the 2.3 kb DNA sequence reacts specifically with all the serotypes of *S. hyodysenteriae* and none of the non-pathogenic intestinal spirochetes further indicates that it may be associated with a virulence determinant of *S. hyodysenteriae* such as hemolysin.

2. Southern blotting.

Approximately 2 μg of chromosomal DNA from *S. hyodysenteriae* serotypes 1 to 7, *S. innocens* isolates B256 and 4/71, WBHIS isolates B359 and B1555a and *T. succinifaciens* were digested with HindIII, electrophoretically separated on a 0.8% agarose gel, and transferred by capillary diffusion as described by Southern et al., *J. Mol. Biol.*, 98:503–517 (1975), to nylon membranes (Hybond™-N, Amersham, Arlington Heights, Ill.). Prehybridization, hybridization, and washing steps with a recombinant DNA fragment (2.3 kb) obtained from the immunopositive clone pRED3C6 labelled with [α-$^{32}$P] dCTP using an oligolabeling kit (Pharmacia LKB Biotechnology, Piscataway, N.J.) were performed as described by Ramanthan et al., *Vet. Microbiol.*, 37:53–64 (1993). For slot blot analysis purified genomic DNAs from cultivable reference isolates of the order Spirochaetales including *S. hyodysenteriae* serotypes 1 through 9, *S. innocens isolates B*256 and 4/71, 16 isolates of WBHIS belonging to 3 genotypic groups distinct from *S. innocens, Spirochaeta aurantia*, Treponema spp., *Borrelia burgdorferi*, and representatives of each of the 10 genetic groups of the family Leptospiraceae, as well as enteric bacteria including *Escherichia coli*, Salmonella spp., Campylobacter spp., and *Bacteroides vulgatus* were applied to nylon membranes (Zeta-probe™, Bio-Rad) using a microfiltration apparatus (Bio-Dot SF®, Bio-Rad). Prehybridization, hybridization and washing steps with a recombinant DNA fragment obtained from the immunopositive clone pRED3C6 labelled with [α-$^{32}$p] dCTP were carried out as described Ramanthan et al., *Vet. Microbiol.*, 37:53–64 (1993). The results are shown in FIG. 2.

Southern blot hybridization of [α-$^{32}$P]dCTP labelled 2.3-kb fragment from clone pRED3C6 yielded a strong hybridization signal with chromosomal DNA from reference isolates of *S. hyodysenteriae* serotypes 1 through 7, but not with *S. innocens* isolates B256 and 4/71, WBHIS isolates B359 and B1555a, and *T. succinifaciens* (FIG. 2). When the same probe was reacted with chromosomal DNAs obtained from other cultivable reference isolates of the order Spirochaetales as well as enteric bacteria including *Escherichia coli*, Salmonella spp., Campylobacter spp., and Bacteroides vulgatus in a slot blot hybridization assay, a specific signal was observed only with chromosomal DNA obtained from reference isolates of *S. hyodysenteriae* serotypes 1 through 9.

3. Primers and internal probe for PCR and Southern blot analysis.

An oligonucleotide primer pair (positive-sense 5'-GGTACAGGCGGAAACAGACCTT (SEQ ID NO:3) and negative-sense 5'-TCCTATTCTCTGACCTACTG (SEQ ID NO:4)) and an internal *S. hyodysenteriae*-specific oligonucleotide probe (positive-sense 5'-TAGGGGCTGCTGTTCTAGCTGTAAATGC (SEQ ID NO:5)) were designed and synthesized (Integrated DNA Technologies, INC. Coralville, Iowa) based on results of DNA sequence analysis of the recombinant DNA fragment of the immunopositive clone pRED3C6. The primers were used for amplification either of purified chromosomal DNAs or total DNA extracted by the method described in Example I and Example V either from normal porcine feces inoculated with *S. hyodysenteriae* cells, or from porcine feces, porcine rectal swabs, and porcine colonic mucosal scrapings obtained from swine with clinical an infection caused by *S. hyodysenteriae*.

Primers or probes can be designed based on the sequence of 2.3 kb HindIII fragment shown in FIG. 1. Primers can be designed using primer search algorithms such as Primer Detective (Clontech Laboratories, Inc., Palo Alto, Calif.). Probes can be designed using OLIGO Computer Program (Rychlik and Rhoades, "A Computer Program for Choosing Optimal Oligonucleotides for Filter Hybridization, Sequencing and In Vitro Amplification of DNA", *Nucleic Acid Res.*, 17:8543–8551 (1989) or other commercially-available computer software with similar applications.

EXAMPLE IV

Analysis of PCR Products from Several Strains of Bacteria

The primers designed as described in Example III were used to amplify either purified chromosomal DNA or total DNA extracted from normal porcine feces inoculated with *S. hyodysenteriae* cells or porcine feces, porcine rectal swabs, and porcine colonic mucosal scrapings obtained from swine with an infection caused by *S. hyodysenteriae*. The PCR products were analyzed by hybridization to an internal probe as described in Example III.

The DNA was amplified using a hot start PCR as described by the manufacturer (GeneAmp™ PCR System 480, Perkin Elmer, Norwalk, Conn.) in a total volume of 75 μl containing 4 mM $MgCl_2$; 1× of PCR buffer; 0.2 mM of each dATP, dCTP, dGTP, dTTP (Perkin-Elmer Cetus); 75 pmol of primers; and 1.5 U of Taq DNA polymerase (Perkin-Elmer Cetus) in sterile filtered autoclaved water. Initial denaturing was for 60 s at 95° C., followed by 30 cycles (60 s at 65° C. and 120 s at 72° C.). The amplified products were visualized in 1.25% agarose gels ran at 3 V/cm and stained with ethidium bromide. Southern blots were prehybridized and hybridized each for 1 hour at $T_m$-10° C. with an internal *S. hyodysenteriae*-specific oligonucleotide probe 5'-end labelled with [γ-$^{32}$P]ATP using T4 polynucleotide kinase (Pharmacia) as described by Maniatis et al., *Molecular Cloning-Laboratory Manual*, Cold Spring Harbor Laboratory, Cold Spring Harbor, N.Y. (1982). Washes consisted of 1× SSPE (3.6M NaCl, 0.2M $NaH_2PO_4$, 0.02M EDTA, pH 7.7) with 0.1% SDS (3 times for 5 min at room temperature and once for 5 min at $T_m$-10° C.). The membranes were exposed to X-OMAT AR Cronex radiograph film (Eastman Kodak Company, Rochester, N.Y.) in a cassette with lightning plus intensifying screens (DuPont, Wilmington, Del.) at −70° C.

Figure 3:
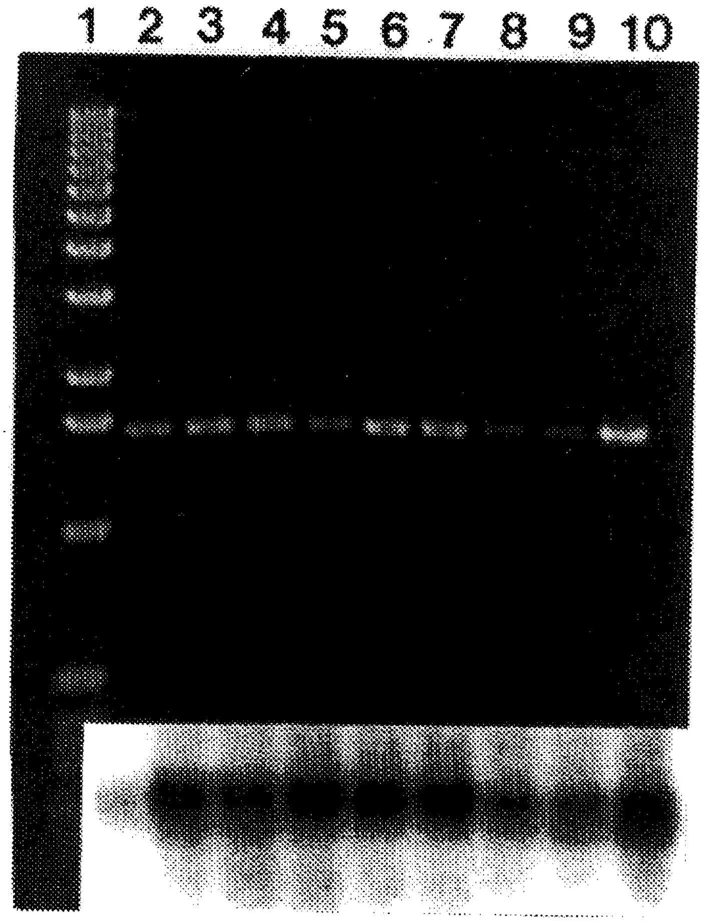
FIG. 3 is a photograph of an ethidium bromide stained agarose gel and Southern blot hybridization of PCR using purified chromosomal DNA obtained from reference isolates of *S. hyodysenteriae* serotypes 1 through 9. The amplified products were electrophoresed on a 0.8% agarose gel and stained with ethidium bromide. The insert at the bottom of the photograph shows hybridization of transferred DNA from the same gel with an internal *S. hyodysenteriae*-specific oligonucleotide probe 5'-end labelled with [γ-$^{32}$P] ATP. Lanes: 1, molecular weight standard (1-kb DNA ladder; GIBCO-BRL); 2, B78; 3, B204; 4, B169; 5, A1; 6, B8044; 7, B6933; 8, AcK 300/8; 9, FM-88-90; 10, FMV 89-3323.
Figure 4:
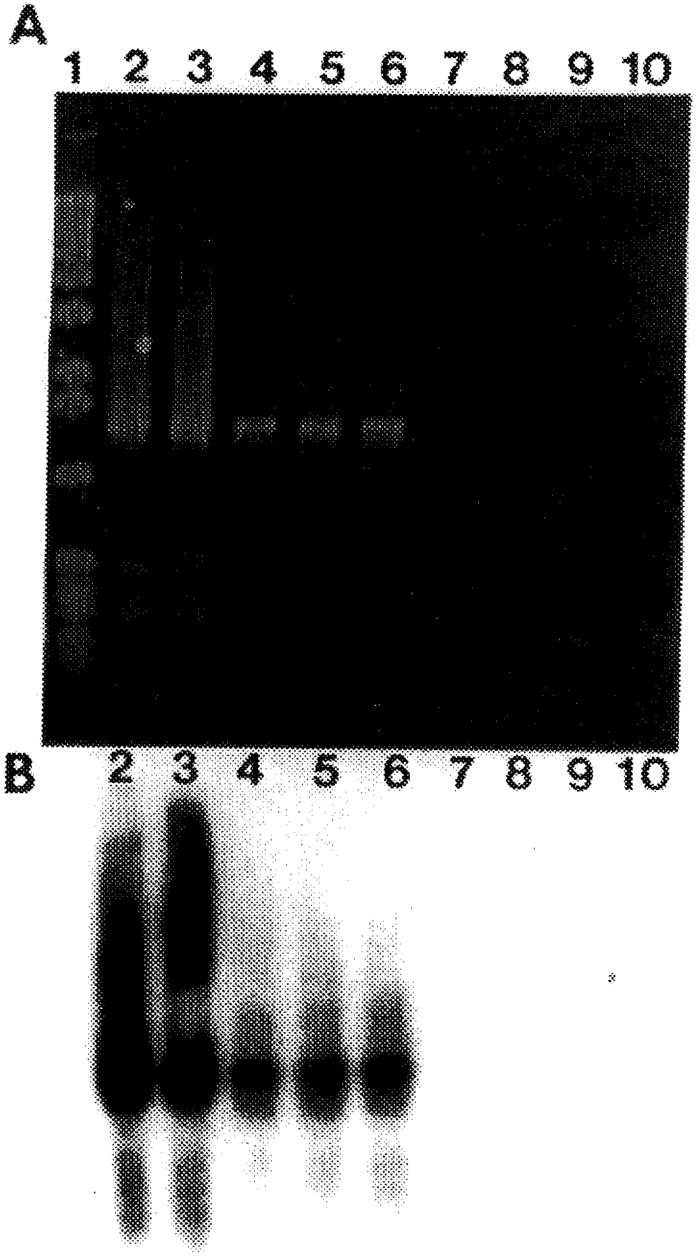
FIG. 4 is a photograph of an ethidium bromide stained agarose gel (panel A) and Southern blot hybridization (panel B) of PCR using purified DNA obtained from porcine feces inoculated with serial ten fold dilutions of Serpulina hyodysenteriae isolate B204 cells.

With purified chromosomal DNA from each of the 9 serotypes of *S. hyodysenteriae* as template, PCR assay resulted in 1.55 kb products (FIG. 3). The specificity of the 1.55 kb products for *S. hyodysenteriae* was confirmed based on production of a restriction endonuclease pattern of the PCR products identical to the predicted restriction map analysis of pRED3C6 (data not shown) and positive hybridization signal with the *S. hyodysenteriae*-specific internal oligonucleotide probe (FIG. 3). The specificity of the reaction for *S. hyodysenteriae* was further confirmed by the absence of products and hybridization signal, respectively after gel electrophoresis and Southern blot hybridization with internal *S. hyodysenteriae*-specific oligonucleotide probe of PCR amplified chromosomal DNA obtained from other cultivable reference isolates of the order Spirochaetales, including *S. innocens* isolates B256 and 4/71, other genotypic groups of WBHIS distinct from *S. innocens*, as well as enteric bacteria including *Escherichia coli*, Salmonella spp., Campylobacter spp., and *Bacteroides vulgatus*.

EXAMPLE V

PCR Detection of *S. hyodysenteriae* from Diagnostic Samples

Samples from uninfected and infected swine were evaluated by the PCR method for diagnosis of the presence of *S. hyodysenteriae*.

1. PCR detection of *S. hyodysenteriae* in porcine feces

The sensitivity of the PCR detection of *S. hyodysenteriae* in porcine feces was determined by two separate methods. In a first method, 10-fold serial dilutions of spirochete broth cultures were added to constant volumes of undiluted normal porcine feces in two separate experiments. The sensitivity of the PCR assay was estimated based on the numbers of spirochete cells in the original culture as determined by a Petroff-Houser cell counting chamber. Briefly, sterile tubes containing 0.1 g of normal feces were inoculated with 1 ml containing either sterile PBS (negative control) or serial ten-fold dilutions of *S. hyodysenteriae* isolate B204 cells in sterile PBS, from $10^5$ to $10^{-2}$ and vortexed for 5 minutes. The samples were allowed to stand for 10 minutes, then the supernatant (approximately 0.9 ml) was drawn off and processed for total DNA extraction as described by the manufacturer (Nucleon DNA extraction kit, Scotlab, Shelton, Conn.) except that the samples were heated at 100° C. for 15 min prior to the cell lysis step and 5M sodium perchlorate deproteinization was replaced by 100 μg of proteinase K per ml. Total DNA from each tube was used for PCR amplification followed by agarose gel electrophoresis and Southern blot analysis using the *S. hyodysenteriae*-specific oligonucleotide probe.

In a second method, feces collected from two untreated swine at the onset of an infection caused by *S. hyodysenteriae* were serially diluted ten-fold ($10^{-1}$ to $10^{-12}$) in 2 ml volumes of sterile PBS. One-ml fractions from each dilution then were processed for determination of the total numbers of viable *S. hyodysenteriae* by a plate counting method, and detection of *S. hyodysenteriae*-specific products by the PCR assay, respectively. For the plate counting method, a total of 10 drops of 10 μl each were placed onto freshly made BJ selective medium, and the number of colony forming units (CFU) per 0.1 ml was determined after incubation at 42° C. in the Gas Pak Anaerobic System (BBL) for 9 days. One ml fractions from each ten-fold dilution were processed for total DNA extraction, and PCR detection of *S. hyodysenteriae*, as described above. The specificity of the PCR assay for detection of *S. hyodysenteriae* in diagnostic specimens was compared with conventional bacteriological culture on BJ medium incubated anaerobically at 42° C. for 10 days. Porcine feces (n=3), porcine rectal swabs (n=2), and porcine colonic mucosal scrapings (n=4) obtained from six different premises where clinical signs of an infection caused by *S. hyodysenteriae* were reported by the referring veterinarians (Duhamel et al., *J. Vet. Diagn. Invest.*, 4:285–292 (1992)), were processed for PCR assays and cultures. For PCR assays, total DNA was extracted from 100 μl of supernatants from either dysenteric porcine feces or porcine colonic mucosal scrapings, as described above. Rectal swabs were mixed with 1 ml of sterile PBS for 2 minutes, and the total DNA was extracted from the supernatants.

Negative controls were included in all PCR assays for detection of *S. hyodysenteriae* in porcine feces. In the spiked feces experiments, unspiked feces and feces spiked with $10^{-2}$ dilution of broth culture (100-fold dilution beyond the numbers of spirochetes estimated by the Petroff-Houser cell counting chamber) were used as negative controls. In the experiments using fecal samples from swine at the onset of an infection caused by *S. hyodysenteriae*, dilutions beyond $10^{-10}$ were considered as negative controls (according to Kunkle et al., *J. Clin. Microbiol.*, 26:2357–2360 (1988), dysenteric feces contain between $10^6$ and $10^{10}$ CFU/g). In the experiments testing diagnostic specimens, the fecal sample containing a WBHIS was used as the negative control.

The sensitivity of the PCR assay for detection of *S. hyodysenteriae* in serial ten-fold dilutions of spirochete broth cultures added to normal porcine feces was 1 organism per 0.1 g of feces in the first experiment (data not shown), and 10 organisms per 0.1 g of feces in the second experiment (FIG. 3). The number of spirochetes in dysenteric feces from 2 untreated swine were comparable to those reported previously for the BJ selective culture medium; $1\times10^5$ and $2\times10^5$ CFU/0.1 ml, respectively. Kunkle et al., *J. Clin. Microbiol.*, 26:2357–2360 (1988). Presence of *S. hyodysenteriae*-specific products at dilutions up to $10^{-9}$ in both fecal specimens by PCR assay indicated a 1,000 fold increase in sensitivity compared with conventional culture. The $10^{-10}$ to $10^{-12}$ dilutions yielded negative results by both methods.

Examination of porcine feces, porcine rectal swabs, and porcine colonic mucosal scrapings obtained from nine swine on six different premises by PCR assays yielded 1.55-kb products in all samples where *S. hyodysenteriae* was identified by conventional bacteriological culture method, as shown in Table III below. The one sample which was negative by PCR assay yielded WBHIS by culture. Table III shows a comparison of conventional bacteriological culture method on selective BJ agar medium and polymerase chain reaction (PCR) assay for detection of *Serpulina hyodysenteriae* in diagnostic specimens.

TABLE III

| | Sample | Result | | |
|---|---|---|---|---|
| Premises | Number | Type | Culture | PCR |
| A | 1 | Feces | *S. hyodysenteriae* | + |
| | 2 | RS† | *S. hyodysenteriae* | + |
| B | 1 | MS | *S. hyodysenteriae* | + |
| C | 1 | MS | *S. hyodysenteriae* | + |
| D | 1 | MS | *S. hyodysenteriae* | + |
| E | 2 | Feces | *S. hyodysenteriae* | + |
| F | 1 | MS | WBHIS | – |
| Total: | 6 | 9 | | |

†RS = Porcine rectal swab.
MS = Porcine colonic mucosal scraping.

EXAMPLE VI

Preparation of Monoclonal Antibodies to *S. hyodysenteriae* Antigens

Monoclonal antibodies were raised against cell-free supernatant antigens from *S. hyodysenteriae* produced by a previously described method (Dupont et al., in press) according to standard methods (Hugo et al., *J. Clin. Microbiol.*, 25:26–30 (1987)). Polyclonal antibodies were raised against two different synthetic peptides selected from the predicted amino acid sequence of the 2.3 kb insert of clone pRED3C6.

1. Monoclonal antibody production.

Eight- to ten-week old BALB/c mice were immunized intraperitoneally with 100 μg of cell-free supernatant antigens from *S. hyodysenteriae*, isolate B204, concentrated 10 times using a YM5 Diaflow ultrafilter (Amicon, Beverly, Mass.) and mixed with equal volumes of Freund's complete adjuvant. Dupont et al., *Vet. Microbiol.*, in press (VETMIC 723). Identical booster injections containing 50 μg of cell-free supernatant antigens in Freund's incomplete adjuvant were given 14, 28, and 42 days later. Four days after the booster injection, spleen cells were harvested and fused with SP 2/0 cells using 50% polyethylene glycol. Hybridomas producing antibodies that reacted with cell-free supernatant antigens from *S. hyodysenteriae*, isolate B204, by ELISA were cloned by limiting dilution and stabilized before injection into mice for ascites production. Hugo et al., *J. Clin. Microbiol.*, 25:26–30 (1987). Monoclonal antibodies 467, F11, 1D8/E11, 3E1D/F1, 6C1D/F8 and 10G6/G10 were identified and are available from Dr. Duhamel, University of Nebraska, Lincoln, Nebr. Hybridoma 10G6/G10 producing an IgM monoclonal antibody that reacted with cell-free supernatant antigens of *S. hyodysenteriae* by ELISA was cloned by limiting dilution and stabilized before injection into mice for ascites production (Hugo et al., cited supra) and is available from Dr. Duhamel, University of Nebraska, Lincoln, Nebr.

2. Polyclonal antibodies to synthetic peptides.

Information on the predicted amino acid sequence encoded by the 2.3 kb fragment of clone pRED3C6 provides a basis for identification of antigenic domains. Using Hopp-Woods hydrophobicity plots as an indicator of surface orientation and potential antigenicity, two peptides were synthesized and used for production of hyperimmune sera in guinea pigs. Hoppet al., *Mol. Immunol.*, 20:483 (1983).

Polyclonal antibodies were produced in adult Hartley Albino guinea pigs against synthetic peptides A (DPAKASRPFD) and B (IPLFEALKPKT) derived from the predicted amino acid sequence of nucleotides 500-529 (peptide A) and 2093-2126 (peptide B) of the 2.3 kb fragment of clone pRED3C6. The initial injection consisted of 50 μg of each peptide diluted in 100 μl of sterile water and mixed with 100 μl of Freund's complete adjuvant administered subcutaneously. Booster injections containing 100 μg of each peptide in 100 μl of sterile water mixed with equal volumes of Freund's incomplete adjuvant were given 14 and 28 days after the initial injection. Final bleeding was completed 7 days after the last booster injection.

EXAMPLE VII

Identification of the Site of *S. hyodysenteriae* Persistence in Carrier Swine A PCR test may be used for screening replacement stock and during herd elimination programs by analyzing fecal shedding patterns by subclinically-infected swine including those on medication as described below.

1. Define the pattern and identify the site of *S. hyodysenteriae* persistence in carrier swine.

About of 20 specific pathogen-free (SPF) swine will be inoculated with *S. hyodysenteriae*, isolate B204, as previously described. Elder et al., cited supra. Each swine will be monitored daily for clinical signs of an infection caused by *S. hyodysenteriae* (usually within 14 days post-inoculation). At least about 30 percent of the swine most likely will die or need to be euthanatized because of severe clinical signs. The remaining naturally-recovered swine will be randomly allocated to two experimental groups and housed in separate isolation rooms of the Pig Research Facility (ARF) of the Department of Veterinary and Biomedical Sciences.

The pattern of *S. hyodysenteriae* shedding in naturally-recovered swine (continuous versus sporadic) will be assessed using the PCR assay described in Example V, and bacterial culture of fecal specimens collected every other day for 30 days from the day of cessation of bloody diarrhea (usually 14 to 21 days after the onset of clinical signs). At the end of 30 days, the effect of stress on fecal shedding of the spirochetes will be determined. Swine from one experimental group will be taken for a 40-mile truck-ride, placed into a disinfected room of the ARF, and the pattern of *S. hyodysenteriae* fecal shedding will be monitored for an additional 7 days.

At the end of the observation period, the swine in each group will be euthanatized and the distribution of *S. hyodysenteriae* in 15 predetermined sites along the wall of the distal ileum, cecum, spiral colon, descending colon, and rectum of each swine will be determined by PCR and culture. Duhamel et al., *J. Vet. Diag. Invest.*, 4:285 (1992) and Elder et al., cited supra. DNA extracted from fecal samples (live swine) and mucosal scrapings (necropsy specimens) obtained from each swine will be subjected to PCR amplification followed by agarose gel electrophoresis and Southern blot analysis using the *S. hyodysenteriae*-specific oligonucleotide probe, as described in Examples IV and V. Results of PCR assay will be compared with conventional bacterial anaerobic culture and will provide an indication of the site of *S. hyodysenteriae* levels in feces and tissues of the swine over time post-infection.

2. Analysis of the pattern of *S. hyodysenteriae* shedding in feces of medicated swine.

A total of 30 SPF swine will be infected with *S. hyodysenteriae*, isolate B204. At the onset of clinical signs, swine will be randomly allocated to five experimental groups of 5 swine each and medicated with the following antimicrobials: Group 1. Carbadox: 50 g/t in feed continuous; Group 2. Tiamulin: 3.5 mg/lb/day in water for 5 days; Group 3.35 g/t in feed continuous; Group 4. Lincomycin: 3.8 mg/lb/day in water for 6 days; Group 5. 100 g/t in feed continuous. The pattern of *S. hyodysenteriae* fecal shedding will be monitored using PCR and bacterial culture every other day for 3 weeks after the initiation of medication. At the end of the observation period, the swine will be euthanatized and the presence of *S. hyodysenteriae* in the intestinal tract of each swine will be determined by PCR and culture. Results will show the efficacy of the treatment regimens to decrease infection with *S. hyodysenteriae* even to very low levels of injection that can be detected by PCR methods.

What is claimed is:

1. A method of detecting the presence of *Serpulina hyodysenteriae* in a biological sample comprising specifically detecting the presence of a DNA sequence from a 2.3 kb HindIII partial digest restriction fragment of *Serpulina hyodysenteriae* B204 corresponding to SEQ ID NO: 1, thereby identifying *Serpulina hyodysenteriae* in the biological sample, if present.

2. A method of detecting the presence of at least one serotype of *Serpulina hyodysenteriae* in one or more biological sample comprising:

(a) amplifying a target sequence of nucleic acids from *Serpulina hyodysenteriae* to form amplification products, wherein the target sequence is at least a portion of a 2.3 kb HindIII partial digest restriction fragment of *Serpulina hyodysenteriae* B204 corresponding to SEQ ID NO: 1;

(b) specifically detecting the amplification products of the target sequence, if present; and (c) thereby detecting *Serpulina hyodysenteriae* in the biological sample, if present.

3. The method according to claim 2, wherein the amplification products are detected by the process comprising:

(a) extracting nucleic acids from the biological sample;

(b) amplifying the target sequence of the extracted nucleic acids using at least one primer that hybridizes to the 2.3 kb HindIII partial digest restriction fragment to provide DNA amplification products of *Serpulina hyodysenteriae;*

(c) specifically detecting the amplification products of the target sequence, if present; and (d) thereby detecting *Serpulina hyodysenteriae* in the biological sample, if present.

4. The method according to claim 2, wherein a DNA amplification product is an about 1.55 kb fragment.

5. The method according to claim 2, wherein the step of amplifying comprises amplifying the target sequence by polymerase chain reaction using at least one primer that hybridizes to the target sequence.

6. The method according to claim 5, wherein the primer has a sequence selected from a group consisting of:

positive-sense 5'-GGTACAGGCGGAAACAGACCTT (SEQ ID NO: 3), negative-sense 5'-TCCTATTCTCTGACCTACTG (SEQ ID NO: 4), complements of these sequences.

7. The method according to claim 5, wherein the step of amplifying comprises:

(a) selecting two primers which each consist of at least 20 contiguous nucleotides selected from one of SEQ ID NO: 1 and its exact complement;

(b) hybridizing said primers with a sample nucleic acid; and (c) performing an amplification reaction to amplify the target *Serpulina hyodysenteriae* 2.3 kb HindIII fragment within the sample.

8. The method according to claim 2, wherein the step of detecting comprises:

(a) contacting DNA amplification products with at least one oligonucleotide probe that hybridizes to the target sequence of the 2.3 kb HindIII partial digest restriction fragment of *Serpulina hyodysenteriae* B204, wherein the probe selection and contacting are under conditions by which said probe will bind to the amplification products of the 2.3 kb HindIII partial digest restriction fragment of *Serpulina hyodysenteriae* to form a hybridization product and will not bind to other DNA sequences and amplification products; and (b) identifying said hybridization product, if present.

9. The method according to claim 8, wherein the probe has the sequence:

sense 5'-TAGGGGCTGCTGTTCTAGCTGTAAATGC (SEQ ID NO: 5).

10. The method according to claim 2, further comprising separating the amplification products.

11. The method according to claim 8, wherein the DNA amplification products are detected by a process selected from a group consisting of dot blot analysis, Southern blot analysis, and multiwell plate analysis.

12. The method according to claim 2, further comprising treating extracted nucleic acids with reverse transcriptase.

13. The method according to claim 2, further comprising placing amplification products from each biological sample of a plurality of biological samples into a different well of a multiwell plate.

14. The method according to claim 8, wherein the probe is detectably labeled.

15. The method according to claim 14, wherein the detectable label is selected from a group consisting of a radioactive nucleotide, biotin labeled nucleotide, flourescent tagged nucleotide and mixtures thereof.

16. The method according to claim 5, wherein the primer is about 16 to about 30 nucleotides long and hybridizes to at least one of the 5' and 3' ends of the target sequence.

17. The method according to claim 5, wherein the primer is a degenerate primer incorporating alternate codon choices for the nucleic acid sequences to be amplified.

18. The method according to claim 1, wherein the biological sample is selected from a group consisting of feces, intestinal contents, mucosal scrapings, and rectal swabs from an animal suspected of being infected with *Serpulina hyodysenteriae.*

19. The method according to claim 1, wherein the biological sample is an environmental sample from a premises suspected of having *Serpulina hyodysenteriae* contamination.

20. The method according to claim 1, further comprising:

(a) digesting DNA in the biological sample with at least one restriction enzyme to form DNA fragments;

(b) contacting said DNA fragments with an oligonucleotide probe that hybridizes to a target DNA sequence of *S. hyodysenteriae* wherein the target sequence is at least a portion of a 2.3 kb HindIII partial digest restriction fragment of *S hyodysenteriae* B 204 corresponding to SEQ ID NO: 1;

(c) wherein the contacting is under conditions by which said probe will hybridize to those of the 2.3 kb HindIII DNA fragments which are complementary to the probe to form a hybridization product and not to other DNA fragments; and (d) identifying said hybridization product, if any.

21. A method for distinguishing at least one serotype of *Serpulina hyodysenteriae* from at least one other microorganism comprising:

(a) amplifying DNA in a biological sample including at least two different microorganisms with at least one primer wherein the primer hybridizes to a 2.3 kb HindIII partial digest restriction fragment target sequence of *Serpulina hyodysenteriae* B204 corresponding to SEQ ID NO: 1;

(b) specifically detecting the amplification products of the *Serpulina hyodysenteriae* target sequence, if present;

(c) if *Serpulina hyodysenteriae* amplification products are present, thereby confirming the presence of *Serpulina hyodysenteriae*; and (d) if no *Serpulina hyodysenteriae* amplification products are present, thereby distinguishing *Serpulina hyodysenteriae* from at least one other microorganism.

22. The method according to claim 21 further comprising:

(a) performing a detection assay for at least one other microorganism on the same biological sample;

(b) specifically detecting the presence of at least one other microorganism, if present;

(c) comparing the results of the detection assays for *Serpulina hyodysenteriae* and at least one other microorganism;

(d) thereby determining whether at least one of *Serpulina hyodysenteriae* and at least one other microorganism is present in the biological sample; and (e) thereby distinguishing *Serpulina hyodysenteriae* from at least one other microorganism.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
( A ) LENGTH: 2332 base pairs
( B ) TYPE: nucleic acid
( C ) STRANDEDNESS: single -continued ( D ) TOPOLOGY: linear ( i i ) MOLECULE TYPE: DNA (genomic)

( i x ) FEATURE:
( A ) NAME/KEY: CDS
( B ) LOCATION: 413..1903

( x i ) SEQUENCE DESCRIPTION: SEQ ID NO:1:

```
CGGCCAGTGC CAAGCTTTAC CAGTTGAGGG CGACTATTAT TCTGATAAAA AAATGTTAAG     60

AAGATTAGAC CCTTTTATTA ATTTTGGAAT ATATGCCGCT CATCATGCAT TTAAGCAGGC    120

TGGTATAGAA CCGAAAACAG GCTTTGATCC TTTAAGAGCC GGTTGTGTTC TTGGTAGCGG    180

TATTGGCGGT ATGACTACTC TTTTATCTAA CCATCAAGTT TTACTTAATG ACGGACCTGG    240

CAGAGTATCA CCTTTCTTTG TACCTATGCA AATAATCAAT ATGACACCTG GTTTAATATC    300

TATGGAATAT GGTATGAACG GACCTAACTA CAGTACAGTT ACTGCATGTG CTTCTTCAAA    360

CCACTCTATA GGTTTAGGTT ATAAACATAT TAAAGATAAT GAAGCTGATA TT ATG        415
                                                          Met
                                                           1

GTA GTT GGA GGT TCT GAA GCT ACT ATA AAT CCT CTT ACT ATA GCT GGT      463
Val Val Gly Gly Ser Glu Ala Thr Ile Asn Pro Leu Thr Ile Ala Gly
              5                  10                  15

TTC AAT AAT GCT AGA GCT TTA TCT ACT AGA AAT GAT GAT CCT GCT AAA      511
Phe Asn Asn Ala Arg Ala Leu Ser Thr Arg Asn Asp Asp Pro Ala Lys
         20                  25                  30

GCA TCA AGA CCT TTT GAT AAA GGA AGA GAC GGA CTT GCT ATA GCC AGA      559
Ala Ser Arg Pro Phe Asp Lys Gly Arg Asp Gly Leu Ala Ile Ala Arg
     35                  40                  45

TAT TTA ATA AAA AAT GGC TAT GAT GTA AAA ATA TAT ATC ACA GGA AAT      607
Tyr Leu Ile Lys Asn Gly Tyr Asp Val Lys Ile Tyr Ile Thr Gly Asn
 50                  55                  60                  65

CTT GAC AGA GTT AAT AAA GAT ACC TAC TCT AAC TTT AAT ATA TTA AAA      655
Leu Asp Arg Val Asn Lys Asp Thr Tyr Ser Asn Phe Asn Ile Leu Lys
                 70                  75                  80

TCT ATG AAT ATA GAT ATT AAT TAT TTA GGA AGC GAA GAA GAT GCC ATA      703
Ser Met Asn Ile Asp Ile Asn Tyr Leu Gly Ser Glu Glu Asp Ala Ile
             85                  90                  95

TCA GCT GCA GAA AAT ATA GAA AGA AAA TCA ATA GTA TTA GAT TCA TTA      751
Ser Ala Ala Glu Asn Ile Glu Arg Lys Ser Ile Val Leu Asp Ser Leu
        100                 105                 110

TTT GGT ACA GGC GGA AAC AGA CCT TTA GAA GGA ATA CAA AAA GCT CTT      799
Phe Gly Thr Gly Gly Asn Arg Pro Leu Glu Gly Ile Gln Lys Ala Leu
    115                 120                 125

ATA GAT AGT TTG AAT AAA TTA GAT GTT CTT AGA ATA GCA ATA GAT ATA      847
Ile Asp Ser Leu Asn Lys Leu Asp Val Leu Arg Ile Ala Ile Asp Ile
130                 135                 140                 145

CCT TCA GGA TTA GCT TCA AAA ATA AAT GAT AAT GAC AAT GTA TAT ACT      895
Pro Ser Gly Leu Ala Ser Lys Ile Asn Asp Asn Asp Asn Val Tyr Thr
                150                 155                 160

TGT TTT AAA GCA CAT GAA ACA TAT ACT ATA TGC TTC GCT AAA GAT ATA      943
Cys Phe Lys Ala His Glu Thr Tyr Thr Ile Cys Phe Ala Lys Asp Ile
            165                 170                 175

TTC TTT TTA TAC AGA ACA AGA GAA TAT ATA GGA AAA TTA TTC ATA ATA      991
Phe Phe Leu Tyr Arg Thr Arg Glu Tyr Ile Gly Lys Leu Phe Ile Ile
        180                 185                 190

AAA TCA ATA TTC CCA GAT GAA ATA TTA GAT AAT TGG GGA TAT AAA GCT     1039
Lys Ser Ile Phe Pro Asp Glu Ile Leu Asp Asn Trp Gly Tyr Lys Ala
    195                 200                 205

AAA CTT ATA GAT TAT AAT GAA AAA ATA AAT ATA AAT AGA AAC TCT CTA     1087
Lys Leu Ile Asp Tyr Asn Glu Lys Ile Asn Ile Asn Arg Asn Ser Leu
```

-continued 210 215 220 225

TAC AGC AAA AGA GAA CAA GGA ATG CTT GCT ATA GTA GCA GGA AGT GAT 1135
Tyr Ser Lys Arg Glu Gln Gly Met Leu Ala Ile Val Ala Gly Ser Asp
230 235 240

AAT TAT ATA GGG GCT GCT GTT CTA GCT GTA AAT GCT GCT TAT AGA TTG 1183
Asn Tyr Ile Gly Ala Ala Val Leu Ala Val Asn Ala Ala Tyr Arg Leu
245 250 255

GGT GTA GGA TAC ATA AGA TTA TAT GTA CCT AAA GGC ATA ATA AAA AAT 1231
Gly Val Gly Tyr Ile Arg Leu Tyr Val Pro Lys Gly Ile Ile Lys Asn
260 265 270

ATA AGA GAT GCC ATA ATG CCT TCT ATG CCT GAA ATT GTT ATT ATA GGA 1279
Ile Arg Asp Ala Ile Met Pro Ser Met Pro Glu Ile Val Ile Ile Gly
275 280 285

GTT GGA GAA GAA AAT CAA AAA TTC TTC ACA GAA AAT GAC ATT GAA ATA 1327
Val Gly Glu Glu Asn Gln Lys Phe Phe Thr Glu Asn Asp Ile Glu Ile
290 295 300 305

GTA AAT GAT ATT AAT AAA AGC GAT GCT TGT ATA ATA GGT TCT GGT ATA 1375
Val Asn Asp Ile Asn Lys Ser Asp Ala Cys Ile Ile Gly Ser Gly Ile
310 315 320

GGC AGA GAT TTG TCT ACA GAA ATT TTT GTA AAT ACT ATA TTA AAG CAA 1423
Gly Arg Asp Leu Ser Thr Glu Ile Phe Val Asn Thr Ile Leu Lys Gln
325 330 335

ATA AAT ATA CCT ACT GTT ATT GAT GCT GAT GCT TTA TAT TTA ATG TTT 1471
Ile Asn Ile Pro Thr Val Ile Asp Ala Asp Ala Leu Tyr Leu Met Phe
340 345 350

GAA AGC ACT CTT AAT GAA CTT AAT AAT AAT TTT ATA ATC ACT CCT CAT 1519
Glu Ser Thr Leu Asn Glu Leu Asn Asn Asn Phe Ile Ile Thr Pro His
355 360 365

ATA TAT GAA TTT GAA AAA CTT ACA CAG ATA AAT CAT ATA GAG GTT TTA 1567
Ile Tyr Glu Phe Glu Lys Leu Thr Gln Ile Asn His Ile Glu Val Leu
370 375 380 385

GAA AAT CCT TAT CAG GCA TTA TTA ATA TAC AGA GAA AAA ACT AAT GCC 1615
Glu Asn Pro Tyr Gln Ala Leu Leu Ile Tyr Arg Glu Lys Thr Asn Ala
390 395 400

TCA ATA GTA TTA AAA GAT GCT GTA AGT TTC CTA ATG CAT GAA AAT GAT 1663
Ser Ile Val Leu Lys Asp Ala Val Ser Phe Leu Met His Glu Asn Asp
405 410 415

ATA TAT ATA AAT TAT AAC CCT AGA GAA TCT ATG GGG AAA GCA GGT ATG 1711
Ile Tyr Ile Asn Tyr Asn Pro Arg Glu Ser Met Gly Lys Ala Gly Met
420 425 430

GGT GAT GTT TTT GCT GGA TTT ATA GGT GCT TTG CTC GCT AGA AAA CTA 1759
Gly Asp Val Phe Ala Gly Phe Ile Gly Ala Leu Leu Ala Arg Lys Leu
435 440 445

AAT ATA TTA GAT GCT TCA AAA CTA GCA TTG ATA ATA CAG GCT AAA TCT 1807
Asn Ile Leu Asp Ala Ser Lys Leu Ala Leu Ile Ile Gln Ala Lys Ser
450 455 460 465

TTT AAT ATA TTA TCA AAA AAA TTC GGA AAT GAT TAT ATT CAG CCT AAA 1855
Phe Asn Ile Leu Ser Lys Lys Phe Gly Asn Asp Tyr Ile Gln Pro Lys
470 475 480

GAT TTG GCA AAT ATT TCA TAT AAA ATA CTA AAA GGA TAT AAA TTT GCC 1903
Asp Leu Ala Asn Ile Ser Tyr Lys Ile Leu Lys Gly Tyr Lys Phe Ala
485 490 495

TAGAGAAGTT TACGACCCTA AACAAAAAGA ATTAGAATTC TACGCTAAAA GAGAGGTAAA 1963

GCCCCCTGCT CCTAAAAGAG AGGTAAGCAT ATTTGCTAGA AGATGGTTTA TGTTTTTATA 2023

CGGAACTTTC CTCACATTAG TTGTAATTGG TATGCTTTTA TATAAAAAAG GATTCTTTAA 2083

TAATATACCA TTATTTGAAG CTTTAAAGCC TAAAACAGAT GTTATAGTAA AAATTAATAA 2143

TGCTGAATTC GTTAATGATG CAGTAATTAC AACTATAGAA CTCGAAAATT CAAATTATAC 2203

-continued

TAATTCTGAA AGTATAGAAA CACTAAGAAG TTATTTTTCA TTGTACAAAA ATAGAAAATT 2263

AATATTTACA GGCAATCGTT CTTTTAATAA TATAAGATTC CCAGTAGGTC AGAGAATAGG 2323

ATTCAATTT 2332

( 2 ) INFORMATION FOR SEQ ID NO:2:

( i ) SEQUENCE CHARACTERISTICS:
( A ) LENGTH: 497 amino acids
( B ) TYPE: amino acid
( D ) TOPOLOGY: linear ( i i ) MOLECULE TYPE: protein ( x i ) SEQUENCE DESCRIPTION: SEQ ID NO:2:

Met Val Val Gly Gly Ser Glu Ala Thr Ile Asn Pro Leu Thr Ile Ala
1 5 10 15

Gly Phe Asn Asn Ala Arg Ala Leu Ser Thr Arg Asn Asp Asp Pro Ala
20 25 30

Lys Ala Ser Arg Pro Phe Asp Lys Gly Arg Asp Gly Leu Ala Ile Ala
35 40 45

Arg Tyr Leu Ile Lys Asn Gly Tyr Asp Val Lys Ile Tyr Ile Thr Gly
50 55 60

Asn Leu Asp Arg Val Asn Lys Asp Thr Tyr Ser Asn Phe Asn Ile Leu
65 70 75 80

Lys Ser Met Asn Ile Asp Ile Asn Tyr Leu Gly Ser Glu Glu Asp Ala
85 90 95

Ile Ser Ala Ala Glu Asn Ile Glu Arg Lys Ser Ile Val Leu Asp Ser
100 105 110

Leu Phe Gly Thr Gly Gly Asn Arg Pro Leu Glu Gly Ile Gln Lys Ala
115 120 125

Leu Ile Asp Ser Leu Asn Lys Leu Asp Val Leu Arg Ile Ala Ile Asp
130 135 140

Ile Pro Ser Gly Leu Ala Ser Lys Ile Asn Asp Asn Asp Asn Val Tyr
145 150 155 160

Thr Cys Phe Lys Ala His Glu Thr Tyr Thr Ile Cys Phe Ala Lys Asp
165 170 175

Ile Phe Phe Leu Tyr Arg Thr Arg Glu Tyr Ile Gly Lys Leu Phe Ile
180 185 190

Ile Lys Ser Ile Phe Pro Asp Glu Ile Leu Asp Asn Trp Gly Tyr Lys
195 200 205

Ala Lys Leu Ile Asp Tyr Asn Glu Lys Ile Asn Ile Asn Arg Asn Ser
210 215 220

Leu Tyr Ser Lys Arg Glu Gln Gly Met Leu Ala Ile Val Ala Gly Ser
225 230 235 240

Asp Asn Tyr Ile Gly Ala Ala Val Leu Ala Val Asn Ala Ala Tyr Arg
245 250 255

Leu Gly Val Gly Tyr Ile Arg Leu Tyr Val Pro Lys Gly Ile Ile Lys
260 265 270

Asn Ile Arg Asp Ala Ile Met Pro Ser Met Pro Glu Ile Val Ile Ile
275 280 285

Gly Val Gly Glu Glu Asn Gln Lys Phe Phe Thr Glu Asn Asp Ile Glu
290 295 300

Ile Val Asn Asp Ile Asn Lys Ser Asp Ala Cys Ile Ile Gly Ser Gly
305 310 315 320

Ile Gly Arg Asp Leu Ser Thr Glu Ile Phe Val Asn Thr Ile Leu Lys
325 330 335

-continued

| | | | | | | | | | | | | | | | |
|---|---|---|---|---|---|---|---|---|---|---|---|---|---|---|---|
| Gln | Ile | Asn | Ile<br>340 | Pro | Thr | Val | Ile | Asp<br>345 | Ala | Asp | Ala | Leu | Tyr<br>350 | Leu | Met |
| Phe | Glu | Ser<br>355 | Thr | Leu | Asn | Glu | Leu<br>360 | Asn | Asn | Asn | Phe | Ile<br>365 | Ile | Thr | Pro |
| His | Ile<br>370 | Tyr | Glu | Phe | Glu | Lys<br>375 | Leu | Thr | Gln | Ile | Asn<br>380 | His | Ile | Glu | Val |
| Leu<br>385 | Glu | Asn | Pro | Tyr | Gln<br>390 | Ala | Leu | Leu | Ile | Tyr<br>395 | Arg | Glu | Lys | Thr | Asn<br>400 |
| Ala | Ser | Ile | Val | Leu<br>405 | Lys | Asp | Ala | Val | Ser<br>410 | Phe | Leu | Met | His | Glu<br>415 | Asn |
| Asp | Ile | Tyr | Ile<br>420 | Asn | Tyr | Asn | Pro | Arg<br>425 | Glu | Ser | Met | Gly | Lys<br>430 | Ala | Gly |
| Met | Gly | Asp<br>435 | Val | Phe | Ala | Gly | Phe<br>440 | Ile | Gly | Ala | Leu | Leu<br>445 | Ala | Arg | Lys |
| Leu | Asn<br>450 | Ile | Leu | Asp | Ala | Ser<br>455 | Lys | Leu | Ala | Leu | Ile<br>460 | Ile | Gln | Ala | Lys |
| Ser<br>465 | Phe | Asn | Ile | Leu | Ser<br>470 | Lys | Lys | Phe | Gly | Asn<br>475 | Asp | Tyr | Ile | Gln | Pro<br>480 |
| Lys | Asp | Leu | Ala | Asn<br>485 | Ile | Ser | Tyr | Lys | Ile<br>490 | Leu | Lys | Gly | Tyr | Lys<br>495 | Phe |
| Ala | | | | | | | | | | | | | | | |

( 2 ) INFORMATION FOR SEQ ID NO:3:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:3:

GGTACAGGCG GAAACAGACC TT 22

( 2 ) INFORMATION FOR SEQ ID NO:4:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:4:

TCCTATTCTC TGACCTACTG 20

( 2 ) INFORMATION FOR SEQ ID NO:5:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:5:

TAGGGGCTGC TGTTCTAGCT GTAAATGC 28